(12) United States Patent
Frutos et al.

(10) Patent No.: US 8,206,908 B2
(45) Date of Patent: *Jun. 26, 2012

(54) **TARGET GENES FOR STRAIN-SPECIFIC DIAGNOSTIC OF *EHRLICHIA RUMINANTIUM* AND USE THEREOF**

(75) Inventors: Roger Frutos, Saint Mathieu de Treviers (FR); Nathalie Vachiery, Lamentin (FR); Thierry Lefrancois, Baie Mahault (FR); Conception Ferraz, Agde (FR); Jacques Demaille, Montferrier-sur-Lez (FR); Dominique Martinez, Sauve (FR)

(73) Assignees: Centre de Cooperation Internationale en Recherche Agronomique Pour le Developpement (Cirad), Paris (FR); Centre National de la Recherche Scientifique, Paris (FR)

( * ) Notice: Subject to any disclaimer, the term of this patent is extended or adjusted under 35 U.S.C. 154(b) by 347 days.

This patent is subject to a terminal disclaimer.

(21) Appl. No.: 12/442,613

(22) PCT Filed: Sep. 25, 2006

(86) PCT No.: PCT/IB2006/003870
§ 371 (c)(1),
(2), (4) Date: Jun. 22, 2009

(87) PCT Pub. No.: WO2008/038062
PCT Pub. Date: Apr. 3, 2008

(65) Prior Publication Data

US 2009/0301880 A1    Dec. 10, 2009

(51) Int. Cl.
*C12Q 1/68*     (2006.01)
*C12P 19/34*    (2006.01)
*C07H 21/02*    (2006.01)
*C07H 21/04*    (2006.01)

(52) U.S. Cl. ....... 435/6.1; 435/91.2; 536/23.1; 536/24.3

(58) Field of Classification Search ................... None
See application file for complete search history.

(56) References Cited

U.S. PATENT DOCUMENTS 5,523,217 A * 6/1996 Lupski et al. ............... 435/91.2
7,919,436 B2 * 4/2011 Frutos et al. ................ 506/14

FOREIGN PATENT DOCUMENTS

WO    WO 2006/045338 A    5/2006

OTHER PUBLICATIONS

Stratagene Catalog, p. 39 (1988).*
International Search Report and Written Opinion for PCT/IB2006/003870 filed Sep. 25, 2006.
Frutos R et al: "Comparative genomic analysis of three strains of *Ehrlichia ruminantium* reveals an active process of genome size plasticity"; Journal of Bateriology 2006 United States, vol. 188, No. 7, Apr. 2006; pp. 2533-2542; XP002430891.

(Continued)

*Primary Examiner* — Teresa E Strzelecka
(74) *Attorney, Agent, or Firm* — Alston & Bird LLP

(57) ABSTRACT

The invention provides a combination of target genes that are useful as genetic markers for the strain-specific detection of *Ehrlichia ruminantium*. The invention also provides diagnostic methods using said combination of markers.

17 Claims, 7 Drawing Sheets

OTHER PUBLICATIONS

Bekker Cornelis P J et al: "Transcription analysis of the major antigenic protein 1 multigene family of three in vitro-cultured *Ehrlichia ruminantium* isolates"; Journal of Bacteriology; vol. 187, No. 14, Jul. 2005, pp. 4782-4791; XP002430892.

Collins Nicola E et al: "The genome of the heartwater agent *Ehrlichia ruminantium* contains multiple tandem repeats of actively variable copy number"; Proceedings of the National Academy of Sciences of the United States of America; vol. 102, No. 3; Jan. 18, 2005; pp. 838-843; XP002430893.

Allsopp M T et al: "*Ehrlichia ruminantium* major antigenic protein gene (map1) variants are not geographically constrained and show no evidence of having evolved under positive selection pressure"; Journal of Clinical Microbiology, Washington, DC, US; vol. 39, No. 11; Nov. 2001; pp. 4200-4203; XP002321870.

\* cited by examiner

TARGET GENES FOR STRAIN-SPECIFIC DIAGNOSTIC OF *EHRLICHIA RUMINANTIUM* AND USE THEREOF

CROSS REFERENCE TO RELATED APPLICATIONS

This application is a national stage application filed under 35 U.S.C. 371 of International Application No. PCT/IB2006/003870, filed September 25, 2006.

FIELD AND BACKGROUND OF THE INVENTION

*Rickettsiae* are intracellular pathogenic bacteria responsible for various diseases on Humans and animals. *Rickettsiae* are transmitted by arthropods, most frequently ticks, lice and mites, and cause major illnesses such as epidemic typhus or Rocky Mountain spotted fever. The genus *Ehrlichia* comprises other species pathogenic for humans and mammals such as *E. chaffeensis*, responsible for Human monocytic ehrlichiosis, *E. canis*, the causing agent of canine monocytic ehrlichiosis.

Another species, *Ehrlichia ruminantium*, formerly known as *Cowdria ruminantium*, is the causing agent of heartwater or cowdriosis, an economically important disease of domestic ruminants. Heartwater can cause up to 80% mortality in susceptible animals. *E. ruminantium* is transmitted by *Amblyomma* ticks and is present in Sub-Saharan Africa and surrounding islands, including Madagascar. Heartwater is also present in several Caribbean islands and is threatening the American mainland.

Vaccination against heartwater has long been based on "infection and treatment". Naïve animals are inoculated with blood containing virulent organisms, a procedure which carries a high risk of uncontrolled clinical reactions and the inadvertent spread of undesirable parasites and viruses. A first generation cowdriosis inactivated vaccine based on cell-cultured derived elementary bodies was developed. Although representing a considerable improvement and the first heartwater vaccine acceptable for widespread use, the level of protection conferred is still not fully satisfactory. Indeed, all animals develop a clinical reaction at challenge despite vaccination. Furthermore, livestock also faces challenge by genetically and antigenically diverse strains.

Diversity of *E. ruminantium* is a key problem which has been recognized for a long time, but insufficient information is available for optimum vaccine formulation and specific diagnostic. Serological diagnostic tests of heartwater using crude antigens from whole bacteria detect false positive reactions due to common antigenic determinants The diversity of *E. ruminantium* was demonstrated at the antigenic level by cross-immunisation studies. Variable antigens were identified by ELISA and immunoblot using cross-absorbed immune sera.

Genetic diversity was later demonstrated when sequencing the Map 1 gene which showed a high degree of sequence heterogeneity concentrated in three hypervariable regions. Genomic polymorphism was also detected using RAPD and RFLP markers. This DNA polymorphism was shown to correlate with antigenic polymorphism.

ELISA-based and serological diagnostics have been developed using the Map 1 and the GroEL (WO 9914233) antigens. Other peptides for serological diagnostic have been described (US 2002004051, US 20020132789, WO 02/066652). Although they have dramatically improved specificity, they still display cross reaction with *E. canis* and *E. chaffeensis*. The map1 gene initially considered as a good marker for geographic diversity, was recently shown not to be geographically constrained. Furthermore, the life span of anti-Map 1 antibodies is rather short.

PCR-based diagnostic methods represent methods of choice for the sensitive and specific detection of *Ehrlichia* in clinically reactive or asymptomatic carrier ruminants, as well as in vectors. However, in the field, hosts and vectors can be co-infested by several parasites and the diversity of pathogen species is further complicated by the existence of extensive intra-species diversity. Thus, it is important to provide means and diagnostic tools allowing not only to identify *E. ruminantium* but also to differentiate between different strains.

Sequences allowing differential diagnostic of *E. ruminantium* strain Gardel and *E. ruminantium* strain Welgevonden have been previously described by the inventors. They have shown, through complete genome sequencing and comparative genomic analysis that several genes were only found in either strain Gardel or strain Welgevonden, without counterpart in the other strain, and that several other genes, while being present in both strains differed between them by one or several mutations, such as large insertions and/or deletions that result in a frameshift and/or in a truncated version of the original gene. These genes were therefore primary targets to develop specific, multitarget diagnostic methods to differentiate between these two strains (WO 2006/045338; Frutos et al., Journal of Bacteriology. 188: 2533-2542, 2006).

SUMMARY OF THE INVENTION

The inventors have now found that the use of a particular combination of some of the target genes described in WO 2006/045338 allowed not only to discriminate between strains Gardel and Welgevonden, but also in a more general way, to detect specifically *E. ruminantium* and to discriminate between a broad range of strains of *E. ruminantium* other than Gardel and Welgevonden including strains for which no genomic sequence data are available.

An object of the invention is thus the use of the following set of genes:
Erum1, defined by the sequence SEQ ID NO: 6
Erum2, defined by the sequence SEQ ID NO: 3
Erum3, defined by the sequence SEQ ID NO: 1
Erum4, defined by the sequence SEQ ID NO: 4
Erum5, defined by the sequence SEQ ID NO: 2
Erum6, defined by the sequence SEQ ID NO: 5
Erum7, defined by the sequence SEQ ID NO: 13
Erum8, defined by the sequence SEQ ID NO: 15
Erum9, defined by the sequence SEQ ID NO: 14
Erum10, defined by the sequence SEQ ID NO: 8,
as targets for the strain-specific detection of *Ehrlichia ruminantium*.

The reference sequences used herein to define the target genes Erum 1-5 and Erum 7-9 are those identified in the Gardel strain; the reference sequences used herein to define the target genes Erum6 and Erum10 are those identified in the Welgevonden strain.

However, it is to be understood that each of these genes actually exists under different allelic forms, depending on the strain of *Ehrlichia ruminantium*. The allelic forms that will be considered herein, having in view strain-specific detection, are in particular those resulting from large insertions and/or deletions that lead to a frameshift or to a truncated version of the original gene.

The invention thus provides a method for the strain-specific detection of *Ehrlichia ruminantium* wherein said method comprises determining, for each of the genes Erum 1 to Erum10 defined above, whether said gene is present in the bacteria to be tested, and under which allelic form.

Advantageously, the method of the invention is carried out by performing PCR amplification of all the target genes Erum 1 to Erum10, and checking, for each of these genes, the presence of one or more amplification product(s), and the size of said amplification product(s).

Within the target genes Erum 1 to Erum10, preferred target regions are as follows:

For Erum 1, the target region can consist of the whole sequence SEQ ID NO: 6, or of a portion thereof; in particular the target region can be defined within the portion spanning from nucleotide 1 to nucleotide 173 of SEQ ID NO: 6.

For Erum 2, the target region can consist of the whole sequence SEQ ID NO: 3, or of a portion thereof; in particular the target region can be defined within the portion spanning from nucleotide 1 to nucleotide 218 of SEQ ID NO: 3.

For Erum 3, the target region can consist of the whole sequence SEQ ID NO: 1, or of a portion thereof; in particular the target region can be defined within the portion spanning from nucleotide 1 to nucleotide 509 of SEQ ID NO: 1.

For Erum 4, the target region can consist of the whole sequence SEQ ID NO: 4, or of a portion thereof; in particular the target region can be defined within the portion spanning from nucleotide 56 to nucleotide 698 of SEQ ID NO: 4.

For Erum 5, the target region can consist of the whole sequence SEQ ID NO: 2, or of a portion thereof; in particular the target region can be defined within the portion spanning from nucleotide 1 to nucleotide 239 of SEQ ID NO: 2.

For Erum 6, the target region can consist of the whole sequence SEQ ID NO: 5, or of a portion thereof; in particular the target region can be defined within the portion spanning from nucleotide 3 to nucleotide 130 of SEQ ID NO: 5.

For Erum 7, a preferred target region is located within the portion spanning from nucleotide 1 to nucleotide 1981 of SEQ ID NO: 13; another preferred target region is located within the portion spanning from nucleotide 2378 to nucleotide 3252 of SEQ ID NO: 13.

For Erum 8, a preferred target region is located within the portion spanning from nucleotide 1 to nucleotide 926 of SEQ ID NO: 15; another preferred target region is located within the portion spanning from nucleotide 1816 to nucleotide 3570 of SEQ ID NO: 15.

For Erum 9, a preferred target region is located within the portion spanning from nucleotide 1 to nucleotide 1307 of SEQ ID NO: 14; another preferred target region is located within the portion spanning from nucleotide 151 to nucleotide 1836 of SEQ ID NO: 14.

For Erum 10, a preferred target region is located within the portion spanning from nucleotide 1 to nucleotide 598 of SEQ ID NO: 8; another preferred target region is located within the portion spanning from nucleotide 792 to nucleotide 3522 of SEQ ID NO: 8; still another target region is located within the portion spanning from nucleotide 599 to nucleotide 791 of SEQ ID NO: 8.

Various techniques for detection of target nucleic acid sequences based on PCR amplification are available in the art.

These methods include in particular combined PCR analysis, i.e. simultaneous gel visualization of ten individual PCR reactions, each one targeting only one of the genes Erum1 to Erum10 defined above. The ten target genes can also be analysed by multiplex PCR, by a single PCR reaction involving simultaneous amplification of all the genes using a mixture of primers and visualization of the pattern on electrophoresis gel, or by a combination of multiplex PCR reactions, each one concerning a subset of the target genes listed above.

Non-limitative examples of PCR primers allowing to carry out the method of the invention are given in Table 2 below. Other suitable PCR primers can easily be designed by one of skill in the art, on the basis of the information provided by the present invention. By way of non-limitative example of oligonucleotide design software suitable for obtaining PCR primers of the invention, one can mention the software Vector NTI Advance 9.0 (Invitrogene).

The invention also comprises diagnostic kits for discriminating between strains of *E. ruminantium* wherein said kits comprise PCR primers for all the target genes Erum 1 to Erum10.

The method of the invention is useful in particular to discriminate between strains of *E. ruminantium* other than strain Gardel and strain Welgevonden. It is also useful to discriminate between strain Gardel and strains of *E. ruminantium* other than strain Welgevonden, or conversely, between strain Welgevonden and strains of *E. ruminantium* other than strain Gardel. Furthermore, it also allows for discriminating between a virulent strain of *E. ruminantium* and its attenuated counterpart.

The method of the invention can be performed either on whole bacteria previously lysed, or on nucleic acid (genomic DNA, cDNA or mRNA) isolated from said bacteria. It is suitable for use at various stages of the life cycle of *E. ruminantium*, more specifically but not limited to the domestic-ruminants infectious stage, vector-interaction stage or reservoir animals-interaction stage. Preferred utilisations of the method of the invention include the detection of *Ehrlichia ruminantium* in a given territory, the strain specific identification of *Ehrlichia ruminantium* in a given territory, the discrimination between strains of *Ehrlichia ruminantium* in a given territory or between different geographical regions, the analysis of strain movements within a region or between geographically distinct regions, the differential presence of strains of *Ehrlichia ruminantium* according to vector species and/or populations or the early detection and risk assessment in regions where potential vectors are present but where the disease has not been recorded yet.

EXAMPLES

Figure 1:
FIGS. 1 to 8 are PCR patterns obtained by gel electrophoresis.
Figure 2:
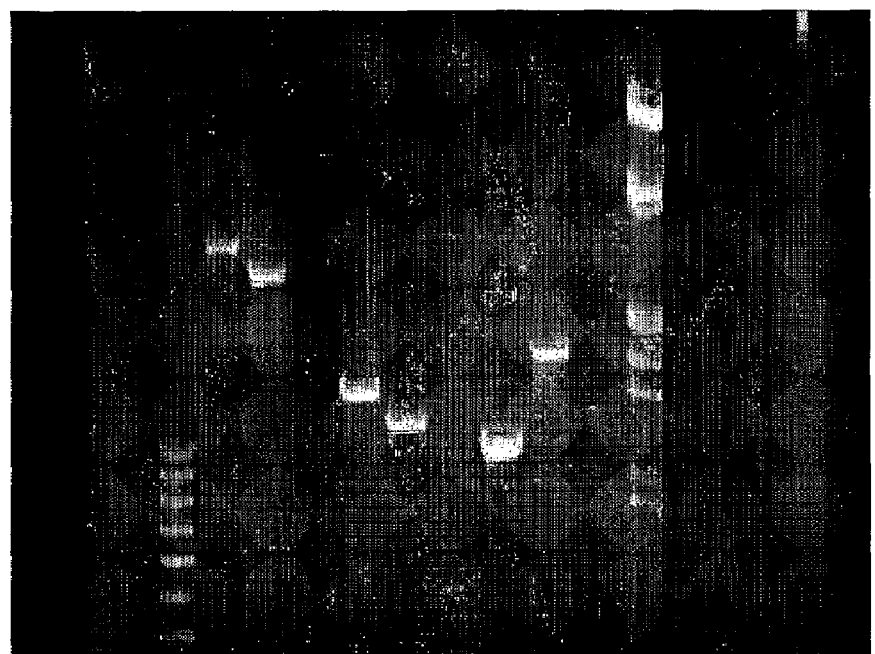

Specifically exemplified herein is the identification of *E. ruminantium* strains based on the specific amplification patterns of the ten target genes defined above.

Example 1

General Features and Sequence Reference

For each strain, purified DNA was broken by sonication to generate fragments of differing sizes. After filling up the ends with Klenow polymerase, DNA fragments ranging from 0.5 kb to 4 kb were separated in a 0.8% agarose gel and collected after gelase (Epicentre) digestion of a cut agarose band. Blunt-end DNA fragments were inserted into pBluescript II KS (Stratagene) digested with EcoRV and dephosphorylated. Ligation was performed with the Fast-Link DNA Ligation kit (Epicentre) and competent DH 10B *E. coli* were transformed prior to colony isolation on LB-agar+Ampicillin+Xgal+ IPTG. About 15000 clones were isolated for each strain of *E. ruminantium*. Plasmidic DNA from recombinant *E. coli* strains was extracted according to the alkaline lysis method and inserts were sequenced on both strands using universal forward and reverse M13 primers and the ET DYEnamic terminator kit (Amersham). Sequences were obtained with ABI 373 et ABI 377 automated sequencers (Applied Biosystems). Data were analysed and contigs were assembled using Phred-Phrap and Consed software packages (http://www-.genome.washington.edu). Gaps were filled in through primer-directed sequencing using custom made primers. A total of about 20000 raw sequence runs were generated and analysed for each *E. ruminantium* strain to generate a full length consensus sequence with a coverage of 6× to 7×.

*E. ruminantium* strain Gardel and *E. ruminantium* strain Welgevonden are virulent pathogenic strains causing heartwater in Guadeloupe Island (French West Indies) and South Africa, respectively. The genome of *E. ruminantium* strains Gardel and Welgevonden is arranged as a circular chromosome of 1499920 bp and 1512977 bp, respectively. The respective G+C contents for the strains Gardel and Welgevonden is 27.51% and 27.48%. The genome of *E. ruminantium* strain Gardel comprises 948 coding sequences of an average size of 1018 bp which represent a total coding surface of 63% of the whole genome. The genome of *E. ruminantium* strain Welgevonden bears 957 genes of the same average size of 1018 bp. The genome surface of this strain devoted to coding sequences is 62%. Both genomes comprise 36 transfer RNAs (tRNA) and 3 ribosomal RNAs (rRNA).

Example 2

Identification of Target Genes for Strain Specific Differential Diagnostic in the Gardel and Welgevonden Strains of *E. Ruminantium*

The differential analysis of the whole genomes of *E. ruminantium* strains Gardel and Welgevonden showed the presence of coding sequences which are present in only one of the strains and not in the other. Some of the CDS which are unique to *E. ruminantium* strain Gardel and found only in the genome of this strain are presented in Table 1 (Seq ID NO 1 to Seq ID NO 5). One of the CDS which is unique to *E. ruminantium* strain Welgevonden and found only in the genome of this strain is presented in Table 1 (Seq ID NO 6). Since these sequences are unique to one or the other strain, they clearly represent targets for the differential detection of *E. ruminantium* strain Gardel versus *E. ruminantium* strain Welgevonden.

The differential analysis of the whole genomes of *E. ruminantium* strains Gardel and Welgevonden also showed the presence of coding sequences which are affected by one or several mutations in one of the two strains and for which a non-mutated, functionally active and normal allele is present in the genome of the other strain. Mutations yielded a stop codon which may result in shorter but still predicted CDS depending upon the size of the remaining fragments. Truncated genes resulting in a single CDS are denominated partial CDS, whereas those resulting in two or more predicted CDS are described as fragmented CDS. These coding sequences are presented in Table 1. One Such CDS in the genome of *E. ruminantium* strain Gardel which is affected by mutations and differs from its native counterpart in *E. ruminantium* strain Welgevonden is presented in Table 1 (SEQ ID NO 7). This is a truncated version of the native gene in *E. ruminantium* strain Welgevonden (Table 1, SEQ ID NO 8). The genome of *E. ruminantium* strain Welgevonden also bears mutated genes, with respect to their allelic variant counterparts in the genome of *E. ruminantium* strain Gardel. Three of these CDS which are affected by mutations generating a truncated version of the genes are presented in Table 1 (SEQ ID NO 9 to SEQ ID NO 12). The native full length allele of these CDS present in the genome of *E. ruminantium* strain Gardel are shown in Table 1 (SEQ ID NO 13 to SEQ ID NO 15). One series of CDS in *E. ruminantium* strain Welgevonden (SEQ ID NO 11 and SEQ ID NO 12), whose native full length alleles are found in the genome of *E. ruminantium* strain Gardel (Table 1, SEQ ID NO 15) was affected by mutations generating a frameshift.

TABLE 1

Target genes for strain-specific differential diagnostic of *E. ruminantium*

| Target gene | Gene in Gardel | Status | Gene in Welgevonden | Status |
|---|---|---|---|---|
| Erum 3 | ERGA_CDS_05600 (SEQ ID No 1) | Unique gene | None | Sequence absent (full deletion) |
| Erum 5 | ERGA_CDS_07600 (SEQ ID No 2) | Unique gene | None | Sequence absent (full deletion) |
| Erum 2 | ERGA_CDS_04990 (SEQ ID No 3) | Unique gene | None | Partial deletion |
| Erum 4 | ERGA_CDS_05610 (SEQ ID No 4) | Unique gene | None | Extensive mutations |
| Erum 6 | None | Partial deletion | ERWE_CDS_08340 (SEQ ID No 5) | Unique gene |
| Erum 1 | ERGA_CDS_04350 (SEQ ID No 6) | Unique gene | None | Extensive mutations |
| Erum 10 | ERGA_CDS_07340 (SEQ ID No 7) | Partial deletion | ERWE_CDS 07420 (SEQ ID No 8) | Full length gene |
| Erum 7 | ERGA_CDS_01350 (SEQ ID No 13) | Full length gene | ERWE_CDS_01390 (SEQ ID No 9) | Partial deletion |

TABLE 1-continued

Target genes for strain-specific differential diagnostic of E. ruminantium

| Target gene | Gene in Gardel | Status | Gene in Welgevonden | Status |
|---|---|---|---|---|
| Erum 9 | ERGA_CDS_05750 (SEQ ID No 14) | Full length gene | ERWE_CDS_05840 (SEQ ID No 10) | Partial deletion |
| Erum 8 | ERGA_CDS_04510 (SEQ ID No 15) | Full length gene | ERWE_CDS_04590 (SEQ ID No 11) ERWE_CDS_04600 (SEQ ID No 12) | Frameshift (partial deletion) |

Example 3

Differential Detection of Strain Gardel and Strain Welgevonden of E. Ruminantium Based on PCR Amplification Patterns of the Target Genes Differential PCR identification of strains Gardel and Welgevonden of E. ruminantium was achieved using primers described in Table 2.

TABLE 2

| Target gene | Primer name | SEQ ID | Orientation | Size (mer) | CDS |
|---|---|---|---|---|---|
| Erum 1 | P-Erum 1-A | SEQ ID #16 | Sense | 21 | ERGA_CDS_04350 |
| Erum 1 | P-Erum 1-B | SEQ ID #17 | Antisense | 21 | ERGA_CDS_04350 |
| Erum 2 | P-Erum 2-A | SEQ ID #18 | Sense | 25 | ERGA_CDS_4990 |
| Erum 2 | P-Erum 2-B | SEQ ID #19 | Antisense | 23 | ERGA_CDS_4990 |
| Erum 3 | P-Erum 3-A | SEQ ID #20 | Sense | 20 | ERGA_CDS_05600 |
| Erum 3 | P-Erum 3-B | SEQ ID #21 | Antisense | 20 | ERGA_CDS_05600 |
| Erum 4 | P-Erum 4-A | SEQ ID #22 | Sense | 19 | ERGA_CDS_05610 |
| Erum 4 | P-Erum 4-B | SEQ ID #23 | Antisense | 22 | ERGA_CDS_05610 |
| Erum 5 | P-Erum 5-A | SEQ ID #24 | Sense | 23 | ERGA_CDS_07600 |
| Erum 5 | P-Erum 5-B | SEQ ID #25 | Antisense | 19 | ERGA_CDS_07600 |
| Erum 6 | P-Erum 6-A | SEQ ID #26 | Sense | 26 | ERWE_CDS_08340 |
| Erum 6 | P-Erum 6-B | SEQ ID #27 | Antisense | 23 | ERWE_CDS_08340 |
| Erum 7 | P-Erum 7-A | SEQ ID #28 | Sense | 25 | ERGA_CDS_01350 ERWE_CDS_01390 |
| Erum 7 | P-Erum 7-B | SEQ ID #29 | Antisense | 25 | ERGA_CDS_01350 ERWE_CDS_01390 ERGA_CDS_04510 |
| Erum 8 | P-Erum 8-A | SEQ ID #30 | Sense | 25 | ERWE_CDS_04590 ERWE_CDS_04600 ERGA_CDS_04510 |
| Erum 8 | P-Erum 8-B | SEQ ID #31 | Antisense | 25 | ERWE_CDS_04590 ERWE_CDS_04600 |
| Erum 9 | P-Erum 9-A | SEQ ID #32 | Sense | 25 | ERGA_CDS_05750 ERWE_CDS_05840 |

TABLE 2-continued

| Target gene | Primer name | SEQ ID | Orientation | Size (mer) | CDS |
|---|---|---|---|---|---|
| Erum 9 | P-Erum 9-B | SEQ ID #33 | Antisense | 25 | ERGA_CDS_05750 ERWE_CDS_05840 |
| Erum 10 | P-Erum 10-A | SEQ ID #34 | Sense | 25 | ERGA_CDS_07340 ERWE_CDS_07420 |
| Erum 10 | P-Erum 10-B | SEQ ID #35 | Antisense | 25 | ERGA_CDS_07340 ERWE_CDS_07420 |

DNA is extracted from elementary bodies of *E. ruminantium*, as described by Perez et al. (1997). *E. ruminantium* strains are grown in BUEC cells as described above. Elementary bodies are purified from the culture supernatant by differential centrifugation and resuspended in 350 μl of PBS to which is added 150 μl of buffer containing 25 mM Tris-HCl (pH 8.0), 10 mM MgCl2 and 125 μg of DNase in order to remove contaminating host cell DNA. After incubation for 90 min. at 37° C., the reaction is stopped by addition of 25 mM EDTA. Elementary bodies are washed three times in water and lysed by overnight incubation at 55° C. in a solution of 100 mM Tris-HCl (pH 8.0), 150 mM NaCl, 25 mM EDTA, 1.5% SDS and 250 μg/ml of proteinase K. Bacterial DNA is extracted with phenol-chloroform, precipitated with cold ethanol an resuspended in sterile distilled water. Contamination with cell DNA is evaluate by slot blot hybridization using labeled bovine DNA as a probe and dilutions of bovine DNA (12.5 ng and 25 ng) as positive controls.

PCR amplification of amplicons is performed by mixing 250 ng of *E. ruminantium* DNA, 2.5 U of Taq DNA polymerase, 200 nM of each dNTP, 1 μM of each, sense and antisense, primer and 3 mM $MgCl_2$ in a final volume of 50 μl. Amplification is done under the following conditions: 5 min denaturation at 94° C., followed by 30 cycles of amplification with a 1-min denaturation, 45 sec of annealing at 45° C. and 2 min extension at 72° C. An extra extension step of 10 min at 72° C. is added after completion of the 30 cycles. PCR products, i.e. amplicons, are analysed by 1% agarose gel electrophoresis in Tris-borate-EDTA buffer.

The results are summarized in Table 3, FIG. 1, and FIG. 2.

Legend of FIG. 1;

1: Molecular weight marker (100-bp ladder); 2: Erga with primers P-Erum 1-A+P-Erum 1-B; 3: Erwe with primers P-Erum 1-A+P-Erum 1-B; 4: Control sample with primers P-Erum 1-A+P-Erum 1-B; 5: Erga with primers P-Erum 2-A+P-Erum 2-B; 6: Erwe with primers P-Erum 2-A+P-Erum 2-B; 7: Control sample with primers P-Erum 2-A+P-Erum 2-B; 8: Erga with primers P-Erum 3-A+P-Erum 3-B; 9: Erwe with primers P-Erum 3-A+P-Erum 3-B; 10: Control sample with primers P-Erum 3-A+P-Erum 3-B; 11: Erga with primers P-Erum 4-A+P-Erum 4-B; 12: Erwe with primers P-Erum 4-A+P-Erum 4-B; 13: Control sample with primers P-Erum 4-A+P-Erum 4-B; 14: Erga with primers P-Erum 5-A+P-Erum 5-B; 15: Erwe with primers P-Erum 5-A+P-Erum 5-B; 16: Control sample with primers P-Erum 5-A+P-Erum 5-B; 17: Erga with primers P-Erum 6-A+P-Erum 6-B; 18: Erwe with primers P-Erum 6-A+P-Erum 6-B; 19: Control sample with primers P-Erum 6-A+P-Erum 6-B; 20: Molecular weight marker (1 EcoRI-HindIII).

Legend of FIG. 2:

1: Molecular weight marker (100-bp ladder); 2: Erga with primers P-Erum 7-A+P-Erum 7-B; 3: Erwe with primers P-Erum 7-A+P-Erum 7-B; 4: Control sample with primers P-Erum 7-A+P-Erum 7-B; 5: Erga with primers P-Erum 9-A+P-Erum 9-B; 6: Erwe with primers P-Erum 9-A+P-Erum 9-B; 7: Control sample with primers P-Erum 9-A+P-Erum 9-B; 8: Erga with primers P-Erum 10-A+P-Erum 10-B; 9: Erwe with primers P-Erum 10-A+P-Erum 10-B; 10: Control sample with primers P-Erum 10-A+P-Erum 10-B; 11: Molecular weight marker (1 EcoRI-HindIII); 12: Molecular weight marker (100-bp ladder); 13: Erga with primers P-Erum 8-A+P-Erum 8-B; 14: Erwe with primers P-Erum 8-A+P-Erum 8-B; 15: Control sample with primers P-Erum 8-A+P-Erum 8-B As shown in Table 3, FIG. 1 and FIG. 2, all the pairs of primers described in Table 3 allowed for differential identification and discrimination of strains Gardel and Welgevonden. The PCR reactions yielded the results expected from in silico prediction of amplicons (Table 3). The pairs P-Erum 1-A+P-Erum 1-B, P-Erum 2-A+P-Erum 2-B, P-Erum 3-A+P-Erum 3-B, P-Erum 4-A+P-Erum 4-B, P-Erum 5-A+P-Erum 5-B, which target unique genes present only in strain Gardel generated the expected unique amplicons of 172 bp, 217 bp, 508 bp, 642 bp and 238 bp, respectively, on strain Gardel while generating no bands on strain Welgevonden (Table 3, FIG. 1). The pair of primers P-Erum 6-A+P-Erum 6-B which target a unique gene only present in strain Welgevonden yielded, as expected, a single amplicon of 127 bp while no PCR product was obtained on strain Gardel (Table 3, FIG. 1). The pairs P-Erum 7-A+P-Erum 7-B, P-Erum 8-A+P-Erum 8-B, P-Erum 9-A+P-Erum 7-B and P-Erum 10-A+P-Erum 10-B targeting the truncated genes yielded PCR products of the respective expected size of 2791 bp, 552 bp+1071 bp, 1361 bp and 1095 bp on strain Gardel and 2395 bp, 492 bp, 1178 bp and 1691 bp on strain Welgevonden, respectively (Table 3, FIG. 2). An additional band of 480 bp is observed on strain Gardel with the pair P-Erum 8-A+P-Erum 8-B. This additional band is most likely due to a single low specificity response occurring in Erga.

The primer pairs P-1350-A+P-1350-B, P-4510-A+P-4510-B, P-5750-A+P-5750-B and P-7420-A+P-7420-B yielded PCR products of the respective expected size of 2791, 552+1071, 1361 and 1095 on strain Gardel and 2395, 492, 1178 and 1691 on strain Welgevonden, respectively (Table 3, FIG. 1 and FIG. 2). An additional band of 480 bp is observed on strain Gardel with the pair P-4510-A+P-4510-B. This additional band is most likely due to a single low specificity response occurring in strain Gardel.

TABLE 3

Strain-specific differential PCR screening of *E. ruminantium* strain Gardel and strain Welgevonden

| | Strain | | | |
|---|---|---|---|---|
| | Gardel | | Welgevonden | |
| Primer combination | Expected | Observed | Expected | Observed |
| P-Erum 1-A + P-Erum 1-B | 172 | 172 | None | None |
| P-Erum 2-A + P-Erum 2-B | 217 | 217 | None | None |
| P-Erum 3-A + P-Erum 3-B | 508 | 508 | None | None |
| P-Erum 4-A + P-Erum 4-B | 642 | 642 | None | None |
| P-Erum 5-A + P-Erum 5-B | 238 | 238 | None | None |
| P-Erum 6-A + P-Erum 6-B | None | None | 127 | 127 |
| P-Erum 7-A + P-Erum 7-B | 2791 | 2791 | 2395 | 2395 |
| P-Erum 8-A + P-Erum 8-B | 552 + 1071 | 552 + 1071 + 480 | 492 | 492 |
| P-Erum 9-A + P-Erum 9-B | 1361 | 1361 | 1178 | 1178 |
| P-Erum 10-A + P-Erum 10-B | 1095 | 1095 + 300 | 1691 | 1691 |

Example 4

Differential Strain-Specific PCR Detection and Identification of Strains of *E. Ruminantium* Different than Strain Gardel and Strain Welgevonden The use primers listed in Table 2 were used for the specific identification and discrimination of *E. ruminantium* strains other than strain Gardel and strain Welgevonden. The strains others than Gardel and Welgevonden presented in this example are strains Umpala (Mozambique), Senegal (Senegal), Bankouma (Burkina Faso), Bekuy (Burkina Faso), Lamba (Burkina Faso), Banan 1 (Burkina Faso) and Banan 2 (Burkina Faso). These strains are presented here to illustrate samples from different parts of Sub-Saharan Africa and the Caribbean.

DNA is extracted from elementary bodies of *E. ruminantium* and PCR amplification performed as described in Example 3.

Figure 3:
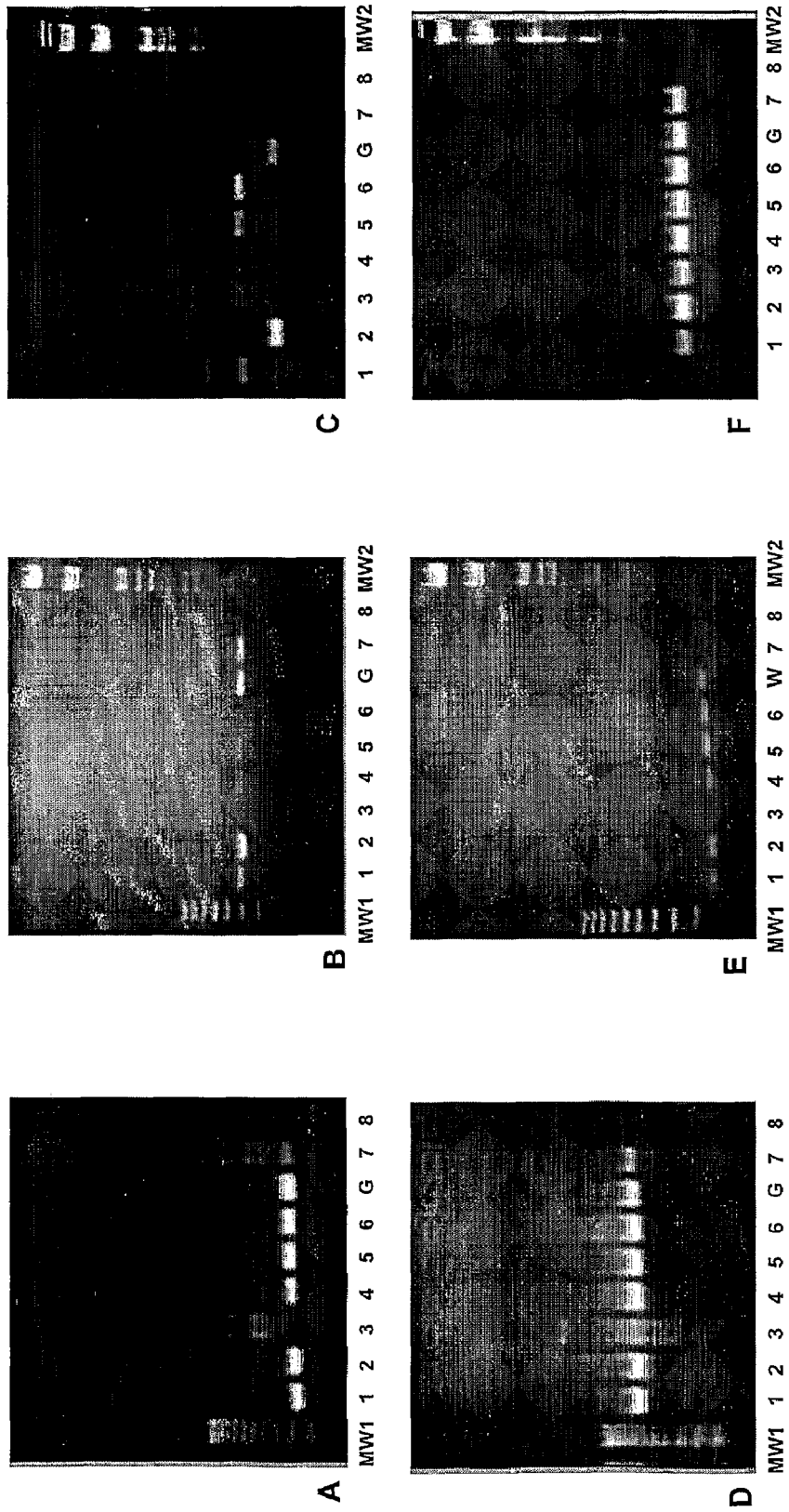
Figure 4:
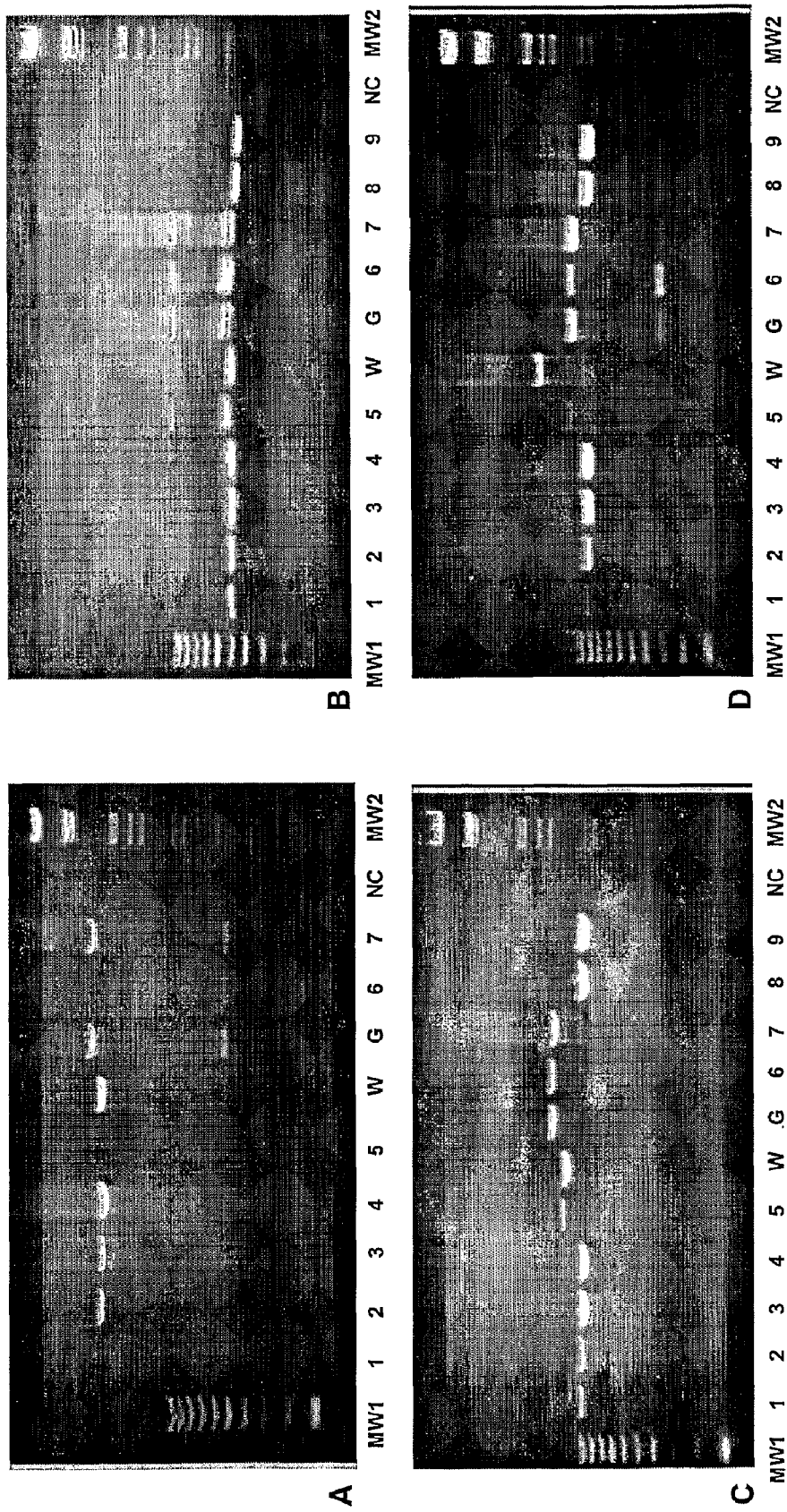

The results are shown in Table 4, FIG. 3 and FIG. 4:

Legend of FIG. 3:

A. PCR detection with primers P-Erum 1-A+P-Erum 1-B

B. PCR detection with primers P-Erum 3-A+P-Erum 3-B

C. PCR detection with primers P-Erum 2-A+P-Erum 2-B

D. PCR detection with primers P-Erum 4-A+P-Erum 4-B

E. PCR detection with primers P-Erum 6-A+P-Erum 6-B

F. PCR detection with primers P-Erum 5-A+P-Erum 5-B

MW1: Molecular weight marker (100 pb DNA ladder); MW2: Molecular weight marker (1 HindIII/EcoRI); 1: Strain Senegal attenuated (Satt); 2: Strain Gardel CTVM; 3: Strain Bankouma; 4: Strain Bekuy; 5: Strain Lamba, 6: Strain Banan 1; 7: Strain Banan 2; NC: Negative control; G. Strain Gardel; W: Strain Welgevonden.

Legend of FIG. 4:

A. PCR detection with primers P-Erum 7-A+P-Erum 7-B

B. PCR detection with primers P-Erum 8-A+P-Erum 8-B

C. PCR detection with primers P-Erum 9-A+P-Erum 9-B

D. PCR detection with primers P-Erum 10-A+P-Erum 10-B

MW1: Molecular weight marker (100 pb DNA ladder); MW2: Molecular weight marker (1 HindIII/EcoRI); 1: Strain Bankouma; 2: Strain Bekuy; 3: Strain Lamba; 4: Strain Banan 1; 5: Strain Banan 2; 6: Strain Gardel attenuated (Gatt); 7: Strain Gardel CTVM; 8: Strain Senegal; 9: Strain Senegal attenuated (Satt); NC: Negative control; G. Strain Gardel; W: Strain Welgevonden.

As shown in Table 4, FIG. 3 and FIG. 4, the combined use of all the pairs of primers described in Table 2 allowed for differential identification and discrimination of strains other than strains Gardel and Welgevonden. The PCR reactions results are summarized in Table 4. The pairs P-Erum 1-A+P-Erum 1-B, P-Erum 2-A+P-Erum 2-B, P-Erum 3-A+P-Erum 3-B, P-Erum 4-A+P-Erum 4-B, P-Erum 5-A+P-Erum 5-B which target unique genes present only in strain Gardel and the pair P-Erum 6-A+P-Erum 6-B which targets a unique gene only present in strain Welgevonden all yielded differing patterns of PCR products depending on the strain (Table 4, FIG. 3). Differing patterns depending upon the strain were also observed using the pairs P-Erum 7-A+P-Erum 7-B, P-Erum 8-A+P-Erum 8-B, P-Erum 9-A+P-Erum 7-B and P-Erum 10-A+P-Erum 10-B which target the truncated genes (Table 4, FIG. 3).

It is however the overall analysis of all the PCR patterns yielded by all the pairs of primers described in Table 2 which provides a strain specific diagnostic. The strains Bekuy and Lamba which were isolated in Burkina Faso from the nearby villages of Bekuy and Lamba, respectively, are most likely to be two isolates of the same strain. Furthermore, these strains display the same map-1 genotype determined by PCR amplification and sequencing of the map-1 gene. All the other strains display differing map-1 genotypes. This further indicates that strains Bekuy and Lamba are two isolate of the same strain. The identical overall pattern obtained for these two strains with all the pairs of primers described in Table 2 also further demonstrate the strain-specificity of the subject of the invention and its ability to identify different strains and separate isolates of the same strain.

TABLE 4

Strain-specific differential PCR screening of *E. ruminantium*

| Primer combination | Gardel | Welgevonden | Umpala | Senegal | Bankouma | Bekuy | Lamba | Banan1 | Banan2 |
|---|---|---|---|---|---|---|---|---|---|
| P-Erum 1-A + P-Erum 1-B | 172 | None | 172 | 172 | Multibands | 172 | 172 | 172 | Multibands |
| P-Erum 2-A + P-Erum 2-B | 217 | None | 515 | 500 + 900 | 280 + 500 + 1200 | 500 + 900 | 500 + 900 | 500 + 900 | 500 + 1200 |
| P-Erum 3-A + P-Erum 3-B | 508 | None | 508 | None | 560 | 508 + 1900 | 508 + 1900 | None | 508 |
| P-Erum 4-A + P-Erum 4-B | 642 | None | 642 | 642 | 642[a] | 642 | 642 | 642 | 642 |
| P-Erum 5-A + P-Erum 5-B | 238 | None | 238 | None | 238 | 238 | 238 | 238 | 238 |
| P-Erum 6-A + P-Erum 6-B | None | 127 | None | 127 | None | 127 | 127 | 127 | None |
| P-Erum 7-A + P-Erum 7-B | 2791 | 2395 | 2791 + 500 | 2395 | 2395 | 2395 | 2395 | 2395 | None |
| P-Erum 8-A + P-Erum 8-B | 552 + 1071 + 480 | 492 | 1200 + 500[a] | 492 | 492 | 492 | 492 | 492 | 552 + 1071 + 480 |
| P-Erum 9-A + P-Erum 9-B | 1361 | 1178 | 1361 | 1000 | 1000 | 1000 | 1000 | 1000 | 1178 + 1361 |
| P-Erum 10-A + P-Erum 10-B | 1095 + 300 | 1691 | 820 | 820 | 820 | 820 | 820 | 820 | 1095 |

[a]presence of additional multiple bands is observed

Example 5

Differential Specific PCR Detection and Identification of Attenuated and Differing Derivates of Strains Gardel and Senegal The primers listed in Table 2 also allow the specific identification of attenuated variants of known strains of *E. ruminantium*.

The following variants were tested:
attenuated derivates of strains Gardel and Senegal denominated Gatt (for Gardel-attenuated) and Satt (for Senegal-attenuated), respectively. The strain Gatt was obtained from the virulent strain Gardel through 248 successive passages BUEC cells whereas strain Satt was obtained from the virulent strain Senegal following 64 passages on BUEC cells. Both the Gatt and Satt strains display an attenuated phenotype characterized by a lack of virulence.

strain Gardel CTVM, which is a subset of strain Gardel maintained in a differing cell environment, and was reported has having undergone mutations in the map1 operon and displaying a diverging phenotype (Bekker et al, 2004).

DNA is extracted from elementary bodies of *E. ruminantium* and PCR amplification performed as described in Example 3.

Figure 5:
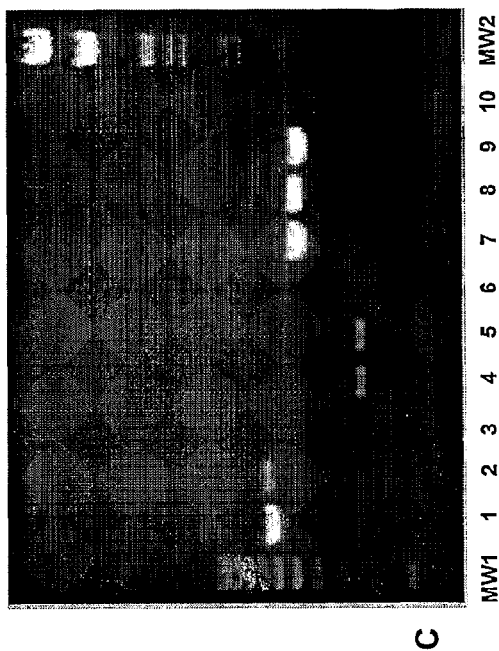
Figure 5:
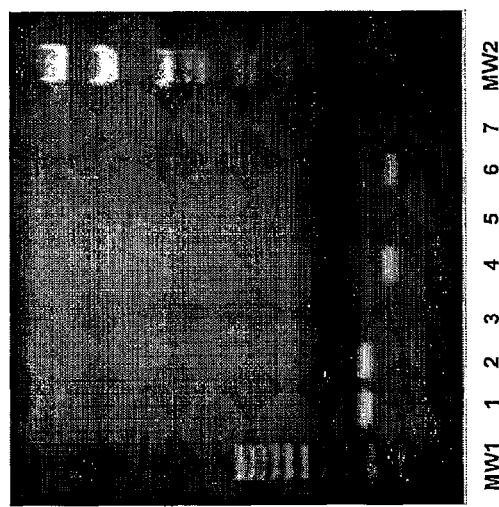
Figure 5:
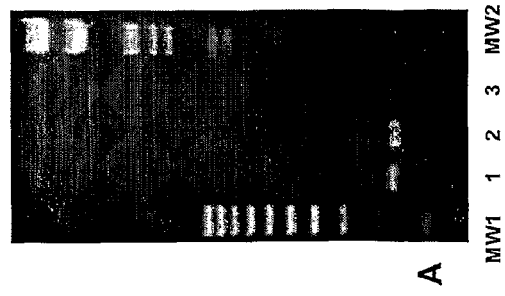

The results are shown in Table 5, FIG. 4, and FIG. 5.

Legend of FIG. 4:
A. PCR detection with primers P-Erum 7-A+P-Erum 7-B
B. PCR detection with primers P-Erum 8-A+P-Erum 8-B
C. PCR detection with primers P-Erum 9-A+P-Erum 9-B
D. PCR detection with primers P-Erum 10-A+P-Erum 10-B
MW1: Molecular weight marker (100 pb DNA ladder); MW2: Molecular weight marker (1 HindIII/EcoRI); 1: Strain Bankouma; 2: Strain Bekuy; 3: Strain Lamba; 4: Strain Banan 1; 5: Strain Banan 2; 6: Strain Gardel attenuated (Gatt); 7: Strain Gardel CTVM; 8: Strain Senegal; 9: Strain Senegal attenuated (Satt); NC: Negative control; G. Strain Gardel; W: Strain Welgevonden.

Legend of FIG. 5:
A. PCR analysis of virulent and attenuated strains with primers P-Erum 1-A+P-Erum 1-B
MW1: Molecular weight marker (100-pb DNA ladder); MW2: Molecular weight marker (1 HindIII/EcoRI); 1: Strain Gardel attenuated (Gatt); 2: Strain Gardel; 3: Negative control.
B. PCR analysis of virulent and attenuated strains with primers P-Erum 2-A+P-Erum 2-B and P-Erum 6-A+P-Erum 6-B
MW1: Molecular weight marker (100-pb DNA ladder); MW2: Molecular weight marker (1 HindIII/EcoRI); Analysis with P-Erum 2-A+P-Erum 2-B of 1: Strain Gardel attenuated (Gatt); 2: Strain Gardel; 3: Negative control; Analysis with P-Erum 6-A+P-Erum 6-B of 4: Strain Gardel attenuated (Gatt); 5: Strain Gardel; 6: Strain Welgevonden; 3: Negative control.
C. PCR analysis of virulent and attenuated strains with primers P-Erum 3-A+P-Erum 3-B, P-Erum 4-A+P-Erum 4-B and P-Erum 5-A+P-Erum 5-B
MW1: Molecular weight marker (100-pb DNA ladder); MW2: Molecular weight marker (1 HindIII/EcoRI); Analysis with P-Erum 4-A+P-Erum 4-B of 1: Strain Gardel attenuated (Gatt); 2: Strain Gardel; 3: Negative control; Analysis with P-Erum 5-A+P-Erum 5-B of 4: Strain Gardel attenuated (Gatt); 5: Strain Gardel; 6: Negative control; Analysis with P-Erum 3-A+P-Erum 3-B of 7: Strain Gardel attenuated (Gatt); 8: Strain Gardel; 9: Strain Gardel; 10: Negative control.

As shown in Table 5, FIG. 4 and FIG. 5, the combined use of all the pairs of primers described in Table 2 also allowed for the differential identification and discrimination of variants and attenuated derivates of known strains. The PCR reactions results are summarized in Table 5. The overall PCR patterns generated on the strain Gardel and two of its derivates, the strain Gardel CTVM and the attenuated strain Gatt show the presence of slight variations—Table 5, FIG. 4, FIG. 5). Furthermore, each strain is characterized by a specific pattern. The strain Gatt differs from the parental virulent strain Gardel by the products from primers pairs P-Erum 6-A+P-Erum 6-B and P-Erum 7-A+P-Erum 7-B, whereas the strain Gardel CTVM differs from the parental strain Gardel by the product from the primers pair P-Erum 6-A+P-Erum 6-B. Similarly, the primers pair P-Erum 7-A+P-Erum 7-B allows for discrimination between the strain Gardel CTVM and the attenuated Gardel strain Gatt. A similar situation is observed between the parental virulent strain Senegal and its attenuated derivate Satt (Table 5, FIG. 4). The virulent strain Senegal and the attenuated strains Satt differ by the PCR product from the primer pairs P-Erum 2-A+P-Erum 2-B, P-Erum 3-A+P-Erum 3-B, P-Erum 6-A+P-Erum 6-B and P-Erum 7-A+P-Erum 7-B.

TABLE 5

Differential identification of attenuated Gardel and Senegal strains of *E. ruminantium*

| Primer combination | Strain | | | | |
|---|---|---|---|---|---|
| | Gardel (Virulent) | Gatt (attenuated Gardel) | Gardel CTVM | Senegal | Satt (attenuated Senegal) |
| P-Erum 1-A + P-Erum 1-B | 172 | 172 | 172 | 172 | 172 |
| P-Erum 2-A + P-Erum 2-B | 217 | 217 | 217 | 500 + 900 | 500 + 900 + 210 |
| P-Erum 3-A + P-Erum 3-B | 508 | 508 | 508 | None | 508 + 1900 |
| P-Erum 4-A + P-Erum 4-B | 642 | 642 | 642 | 642 | 642 |
| P-Erum 5-A + P-Erum 5-B | 238 | 238 | 238 | None | 238 |
| P-Erum 6-A + P-Erum 6-B | None | 127 | 127 | 127 | 127 |
| P-Erum 7-A + P-Erum 7-B | 2791 | None | 2791 | 2395 | 2395 + 700 + 300 |
| P-Erum 8-A + P-Erum 8-B | 552 + 1071 + 480 | 552 + 1071 + 480 | 552 + 1071 + 480 | 492 | 492 |
| P-Erum 9-A + P-Erum 9-B | 1361 | 1361 | 1361 | 1000 | 1000 |
| P-Erum 10-A + P-Erum 10-B | 1095 + 300 | 1095 + 300 | 1095 + 300 | 820 | 820 |

Example 6

Absence of Cross-Reaction with Other Rickettsiales

To verify the specificity assessment of the primers listed in Table 2, they were tested on Rickettsiales belonging to other species and genera than *E. ruminantium* i.e. *Ehrlichia canis*, *Anaplasma platys* and *Anaplasma marginale*.

DNA extraction and PCR amplification were performed as described in Example 3.

Figure 6:
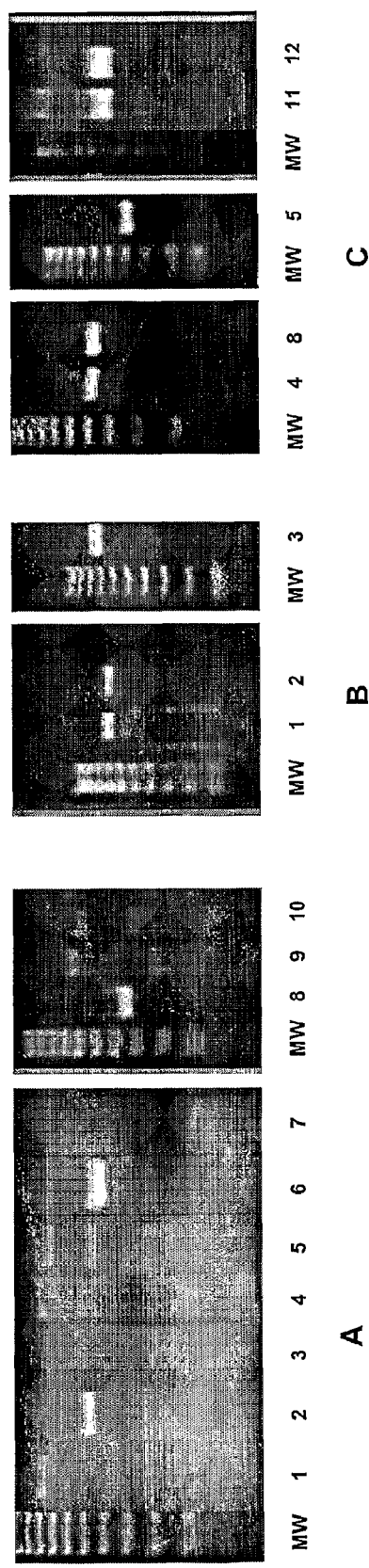
Figure 7:
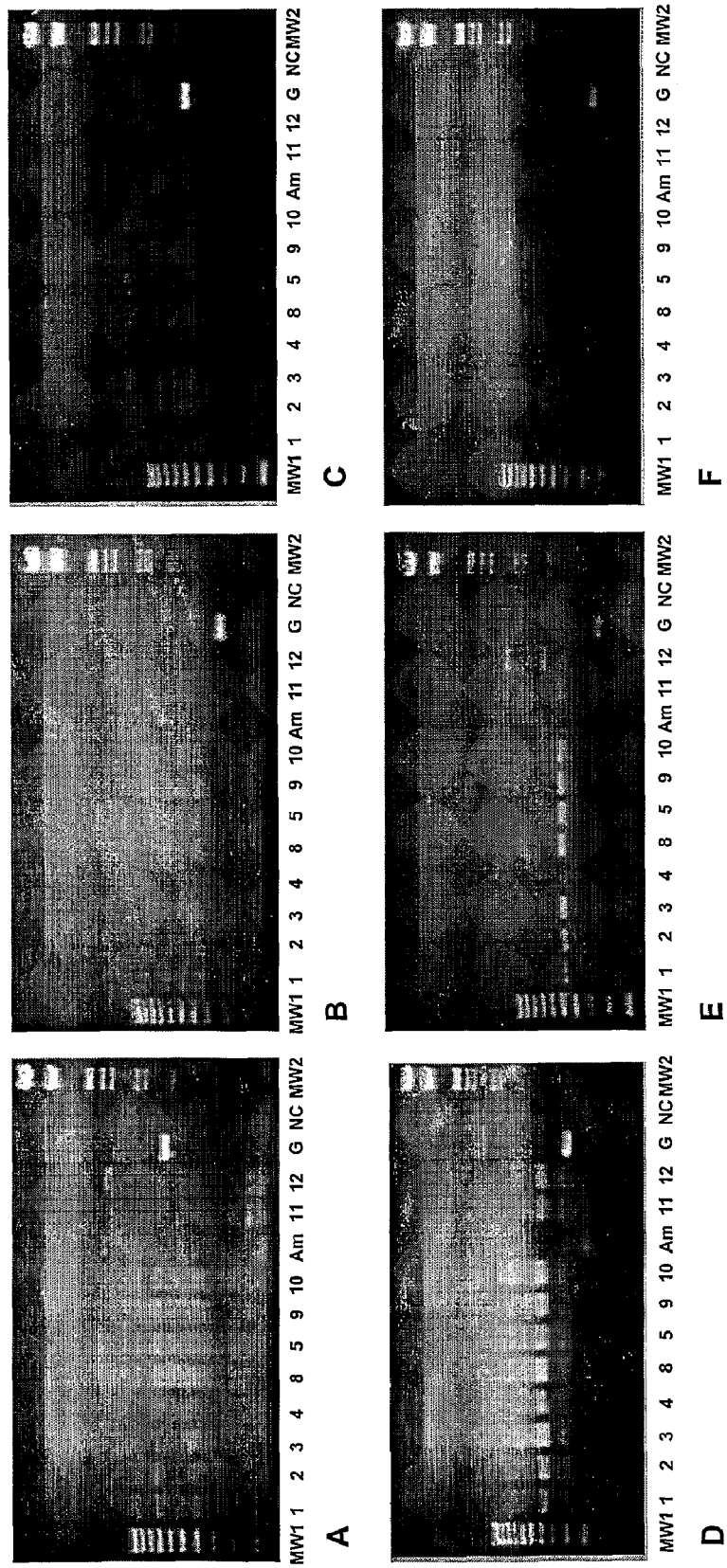
Figure 8:
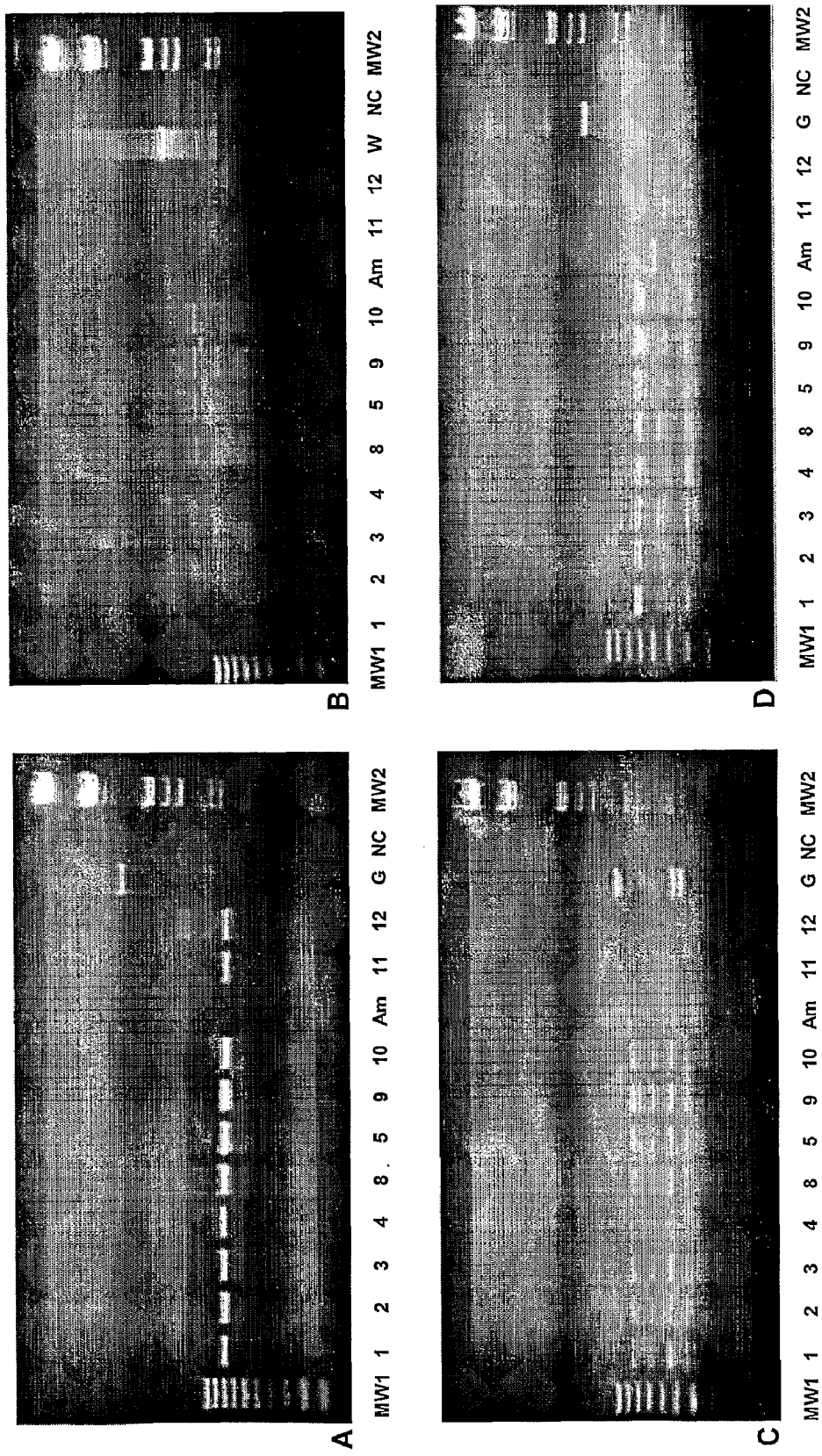

The results are shown in FIGS. 6, 7, and 8.

Legend of FIG. 6:
  A. PCR detection with probe EHR16S specific to *Ehrlichia* spp. 16S rDNA MW: Molecular weight marker (100-bp ladder); 1, 2 and 3: DNA isolated from blood samples from dogs infected with *Anaplasma platys*, 4, 5 and 8: DNA isolated from blood samples from dogs infected with *Ehrlichia canis*; 6: *Ehrlichia canis* positive control; 7: Negative control; 9 and 10: Control DNA isolated from blood samples from non-infected dogs.
  B. PCR detection with Nested PCR probes specific to *Anaplasma platys*

MW: Molecular weight marker (100-bp ladder); 1, 2 and 3: DNA isolated from blood samples from dogs infected with *Anaplasma platys*.
  C. PCR detection with Nested PCR probes specific to *Ehrlichia canis*

MW: Molecular weight marker (100-bp ladder); 4, 5 and 8: DNA isolated from blood samples from dogs infected with *Ehrlichia canis*; 11: DNA from canine monocytes cultures infected with *E. canis* (supernatant); 12: DNA from canine monocytes cultures infected with *E. canis* (pellet).

Legend of FIG. 7:
  A. PCR detection with primers P-Erum 1-A+P-Erum 1-B
  B. PCR detection with primers P-Erum 2-A+P-Erum 2-B
  C. PCR detection with primers P-Erum 3-A+P-Erum 3-B
  D. PCR detection with primers P-Erum 4-A+P-Erum 4-B
  E. PCR detection with primers P-Erum 5-A+P-Erum 5-B
  F. PCR detection with primers P-Erum 6-A+P-Erum 6-B MW1: Molecular weight marker (100 pb DNA ladder); MW2: Molecular weight marker (1 HindIII/EcoRI); 1, 2 and 3: DNA isolated from blood samples from dogs infected with *Anaplasma platys*, 4, 5 and 8: DNA isolated from blood samples from dogs infected with *Ehrlichia canis*; 9 and 10: Control DNA isolated from blood samples from non-infected dogs, 11: DNA from canine monocytes cultures infected with *E. canis* (supernatant); 12: DNA from canine monocytes cultures infected with *E. canis* (pellet); Am: DNA from *Anaplasma marginale*; G: DNA from strain Gardel; NC: Negative control.

Legend of FIG. 8:
  A. PCR detection with primers P-Erum 7-A+P-Erum 7-B
  B. PCR detection with primers P-Erum 8-A+P-Erum 8-B
  C. PCR detection with primers P-Erum 9-A+P-Erum 9-B
  D. PCR detection with primers P-Erum 10-A+P-Erum 10-B MW1: Molecular weight marker (100 pb DNA ladder); MW2: Molecular weight marker (1 HindIII/EcoRI); 1, 2 and 3: DNA isolated from blood samples from dogs infected with *Anaplasma platys*, 4, 5 and 8: DNA isolated from blood samples from dogs infected with *Ehrlichia canis*; 9 and 10: Control DNA isolated from blood samples from non-infected dogs, 11: DNA from canine monocytes cultures infected with *E. canis* (supernatant); 12: DNA from canine monocytes cultures infected with *E. canis* (pellet); Am: DNA from *Anaplasma marginale*; G: DNA from strain Gardel; W: DNA from strain Welgevonden; NC: Negative control.

FIG. 6 indicates that the samples used indeed contain DNA from *A. platys* and *E. canis* as demonstrated by their recognition by 16S rDNA-specific primers and primers for nested PCR specific to each species. As shown in FIG. 7 and FIG. 8, the pairs of primers described in Table 2 are strictly specific to *E. ruminantium* and display no cross-reaction with other related Rickettsiales since no specific PCR product could be detected on *E. canis, A. platys* and *A. marginale* (FIG. 7 and FIG. 8). Whereas no PCR products are detectable on whatever pair of primers was used, PCR products were visible on *A. platys* and *E. canis*. However, all these PCR products are generated by cross-reactions with canine blood cells as shown by the detection of these same bands on non-infected canine cells (FIG. 7 and FIG. 8). This demonstrate that the primers described in Table 2 and targeting the target genes described in Table 1 allow for specific identification of *E. ruminantium* and discrimination between strains of *E. ruminantium* even when other Rickettsiales are present.

The tools provided by the invention allow thus both for specific detection of *E. ruminantium*, even in presence of contaminating related Rickettsiales, for specific discrimination between different strains of *E. ruminantium* and for specific discrimination between a virulent strains and its vaccinal attenuated derivates. This in turn allows for monitoring of vaccination.

The invention claimed is:

1. A method for the strain-specific detection of *Ehrlichia ruminantium* wherein said method comprises determining, for each of the following set of target genes:
- Erum1, defined by the sequence SEQ ID NO: 6
- Erum2, defined by the sequence SEQ ID NO: 3
- Erum3, defined by the sequence SEQ ID NO: 1
- Erum4, defined by the sequence SEQ ID NO: 4
- Erum5, defined by the sequence SEQ ID NO: 2
- Erum6, defined by the sequence SEQ ID NO: 5
- Erum7, defined by the sequence SEQ ID NO: 13
- Erum8, defined by the sequence SEQ ID NO: 15
- Erum9, defined by the sequence SEQ ID NO: 14
- Erum10, defined by the sequence SEQ ID NO: 8, whether said gene is present in a sample of bacteria to be tested.

2. A method for the strain-specific detection of *Ehrlichia ruminantium* wherein said method comprises detecting, for each of the genes Erum1 to Erum10,
- Erum1, defined by the sequence SEQ ID NO: 6
- Erum2, defined by the sequence SEQ ID NO: 3
- Erum3, defined by the sequence SEQ ID NO: 1
- Erum4, defined by the sequence SEQ ID NO: 4
- Erum5, defined by the sequence SEQ ID NO: 2
- Erum6, defined by the sequence SEQ ID NO: 5
- Erum7, defined by the sequence SEQ ID NO: 13
- Erum8, defined by the sequence SEQ ID NO: 15
- Erum9, defined by the sequence SEQ ID NO: 14
- Erum10, defined by the sequence SEQ ID NO: 8, whether an allele of said gene is present in the bacteria to be tested, and determining the form of said allele.

3. A method according to claim 2, which comprises performing PCR amplification of all the target genes Erum 1 to Erum10, and checking, for each of these genes, the presence of one or more amplification product(s), and the size of said amplification product(s).

4. A method according to claim 3 wherein said step of performing PCR amplification comprises simultaneous gel visualization of ten individual PCR reactions, each one targeting only one of the genes Erum1 to Erum10.

5. A method according to claim 3, wherein said step of performing PCR amplification comprises a single PCR reaction involving simultaneous amplification of all the genes using a mixture of primers and visualization of the pattern on electrophoresis gel.

6. A method according to claim 1, wherein for target genes Erum 1 to Erum 6, the target region is the whole sequence.

7. A method according to claim 1, wherein for target gene Erum 1 the target region is within the portion spanning from nucleotide 1 to nucleotide 173 of SEQ ID NO: 6.

8. A method according to claim 1, wherein for target gene Erum 2 the target region is within the portion spanning from nucleotide 1 to nucleotide 218 of SEQ ID NO: 3.

9. A method according to claim 1, wherein for target gene Erum 3 the target region is within the portion spanning from nucleotide 1 to nucleotide 509 of SEQ ID NO: 1.

10. A method according to claim 1, wherein for target gene Erum 4 the target region is within the portion spanning from nucleotide 56 to nucleotide 698 of SEQ ID NO: 4.

11. A method according to claim 1, wherein for target gene Erum 5 the target region is within the portion spanning from nucleotide 1 to nucleotide 239 of SEQ ID NO: 2.

12. A method according to claim 1, wherein for target gene Erum 6 the target region is within the portion spanning from nucleotide 3 to nucleotide 130 of SEQ ID NO: 5.

13. A method according to claim 1, wherein for target gene Erum 7 the target region is within the portion spanning from nucleotide 1 to nucleotide 1981 of SEQ ID NO: 13; or within the portion spanning from nucleotide 2378 to nucleotide 3252 of SEQ ID NO: 13.

14. A method according to claim 1, wherein for target gene Erum 8 the target region is within the portion spanning from nucleotide 1 to nucleotide 926 of SEQ ID NO: 15; or within the portion spanning from nucleotide 1816 to nucleotide 3570 of SEQ ID NO: 15.

15. A method according to claim 1, wherein for target gene Erum 9 the target region is within the portion spanning from nucleotide 1 to nucleotide 1307 of SEQ ID NO: 14; or within the portion spanning from nucleotide 151 to nucleotide 1836 of SEQ ID NO: 14.

16. A method according to claim 1, wherein for target gene Erum 10 the target region is within the portion spanning from nucleotide 1 to nucleotide 598 of SEQ ID NO: 8; or within the portion spanning from nucleotide 792 to nucleotide 3522 of SEQ ID NO: 8; or within the portion spanning from nucleotide 599 to nucleotide 791 of SEQ ID NO: 8.

17. A diagnostic kit for discriminating between strains of *E. ruminantium* wherein said kit comprises PCR primers for all the following set of target genes Erum 1 to Erum10:
- Erum1, defined by the sequence SEQ ID NO: 6
- Erum2, defined by the sequence SEQ ID NO: 3
- Erum3, defined by the sequence SEQ ID NO: 1
- Erum4, defined by the sequence SEQ ID NO: 4
- Erum5, defined by the sequence SEQ ID NO: 2
- Erum6, defined by the sequence SEQ ID NO: 5
- Erum7, defined by the sequence SEQ ID NO: 13
- Erum8, defined by the sequence SEQ ID NO: 15
- Erum9, defined by the sequence SEQ ID NO: 14
- Erum10, defined by the sequence SEQ ID NO: 8.

* * * * *

SEQUENCE LISTING

<160> NUMBER OF SEQ ID NOS: 35

<210> SEQ ID NO 1
<211> LENGTH: 630
<212> TYPE: DNA
<213> ORGANISM: Ehrlichia ruminantium

<400> SEQUENCE: 1

```
atgaaaggat ctttatctgc taaagttatt tctgaaaatc taccattagt agagatggaa      60
aaagcagttc ttagtcctac tgctcgtatt tttctcacta atcataagtt gggacctgtc     120
atggaccttg gaatttatat cttaatacat catagtaatc ttcgtttatt aacgaaggaa     180
aacctttatc ctgctaataa cctaagtaaa attggtaaag tggtgctttg taaacctttg     240
tctataggca atggcataca tacagtacat atgtacttta atgaactcga agctttaaaa     300
gaattcggag gattagaaaa tgctcgcttt acaacagtac gtccggactc cccttgcat      360 acacatacat ctaaaaaaaa gaaatcatta tttacaaaac gttcagatac ttgctataca     420
ctattatgtg aggaatctta tacagatcca aataataccg aaactgatag tacagtaaaa     480
gcaatatcac ataatgaaga agaagaaggt gcagtaagag gagatatacc acaatatcaa     540
ctttccaatg ccgaagcact aggtcgtggt cttgcttttt tccatgatgt tgcaagtaat     600
tttgaaacat tatgcagaag ataccattaa                                      630
```

<210> SEQ ID NO 2
<211> LENGTH: 303
<212> TYPE: DNA
<213> ORGANISM: Ehrlichia ruminantium

<400> SEQUENCE: 2

```
atggatttaa ataaactaat aaagagatta gtattttcat ttgtaatgat taattttgtt      60
aataggtttt ttagtaatac agaaagtgaa agcttgcatt taagtgatag tttacgacat     120
tattattatt ttctatgttt gtgccatgca gtaatggggt ttattatagt aaatacagat     180
ggatataaca tccttgagga ttttatgttc tcagaacaaa tcgtaggtag agaaaatgca     240
gaaatgcttt caatatcaga tacagagggg ggggggggag agcttagtag aagaaaattc     300
tag                                                                   303
```

<210> SEQ ID NO 3
<211> LENGTH: 270
<212> TYPE: DNA
<213> ORGANISM: Ehrlichia ruminantium

<400> SEQUENCE: 3

```
atgtatttag tctatttagt agctggtttt gtggtactat atagtaatta tcgagatata      60
```

```
aattatgata aaaaacttgc tattctttat tctaggggag aagatgatga atataaatat    120
gttcctagga aagagcagaa taatcaatat tattttcata taaaattgta tagtgttaag    180
ttaaatttaa tgtcagatat tgttcaatta gatgttataa tgttaaaagg attttattat    240
agcaatatgt ttaatgtctt tttattttaa                                     270
```

```
<210> SEQ ID NO 4
<211> LENGTH: 828
<212> TYPE: DNA
<213> ORGANISM: Ehrlichia ruminantium

<400> SEQUENCE: 4
gtgtgttact taattggtaa ttttatgtta ttcaaataca atcctcaaaa tactaaagaa     60
ttacatgatg cagctttaaa ttgtttacgt catacaagat tatatgcata tagctaccgt    120
tgtataggac atactgaacc taatggaaca ctacatgtat tcataagtaa agataaatca    180
aataatttgt gtttaccaaa agaagggtat tctctattct atatagaatg tagtctatct    240
gataagagag tatctcagaa tcaggaaata agagatatga tgcaagcagt tgtccgccac    300
aaaattaacc gccttgcttt taataaccct cacacgacac ctaccataga tgtaggcatt    360
tatattttaa taaataaaag taaccttaat atgttaacaa agaacatat aacacctacc    420 aacaacatgg acagtgttgg ccatatgata ttatgcaaac ctgtacgtgc agctaatggt    480
ttactctcat tagacttcct attcaatgaa gaagaagctt taaaagagct tggaggatta    540
caaaatgcag tatttacgat aatagaaact acaccaccta ttaccaaaaa atcattattc    600
agaagacatt cactgggtta ttcacaacta tcagaagaac atagtaaacc tgaaacaatt    660
accagtagta ctattacaga gagtataaca agagaagaag cacaatcaag taaacaagag    720
gaaggattag aaacacatca gctttccacc aatgtagtaa cacatggtat caattattta    780
actaatgtct cacttgcttt tgaacagcta tgtacaaaat atcattaa                 828
```

```
<210> SEQ ID NO 5
<211> LENGTH: 225
<212> TYPE: DNA
<213> ORGANISM: Ehrlichia ruminantium

<400> SEQUENCE: 5
ttgtacatag tatgtcttta tataaaagta agaattgatg attctactga tgttattact     60
tataactcta aaaaaaatat gtgtaaatta caattaactc agaaaaagaa tagatcattt    120
atatatttgg ttaacagata ctatcataaa tcagaatata ggcttaccac actttcagtt    180 caatccttata gcaaattaga gcaactttat aacaatatcc agtaa                    225
```

```
<210> SEQ ID NO 6
<211> LENGTH: 186
<212> TYPE: DNA
<213> ORGANISM: Ehrlichia ruminantium

<400> SEQUENCE: 6
atgagtcaca gttttattga gtttaaacaa atcaattatt acgatattaa cgcaatatat     60
acaatatcat ttgtaacaca tatcaataat tttataccaa aatataagag aaaaattatt    120
ataactctgc ttaatacact aattaacaat attacttctt gtgatttga gtgtaataaa    180 caatga                                                                186
```

```
<210> SEQ ID NO 7
<211> LENGTH: 3522
```

<210> TYPE: DNA
<213> ORGANISM: Ehrlichia ruminantium

<400> SEQUENCE: 7

```
atgaatgaga taatcctata cacagcagtg tcgctgtttt ttatatgtgt ttactatgtt      60
ctgcttgtgg ttaggtttgt atgttatgtg ttgagtgtta tgaagtataa gtcaaaggaa     120
ttggacatat cagataatta tacaaaaagt agggttactt attgtagtca gagtgaatat     180
gaaaagtacg aaatggacac tttatctgga aaagatggta ttgaatttct aaaatcagtt     240
taccataatg atagtgatga tataggtcat gttttaaaat caaaatctac tgtttcatct     300
accaaaatgg atcaggtaac acatcaagtt cctggcgttc aaactataga acacgatagt     360
gcgatagaag gtcaccaagt tatggataag gaaaatgctg gtgttggtgt tcactatagt     420
catactgaaa ctactataaa aacaagtctt agttttaaat ctgatgttat ggttgatact     480
aaggataaat ctgtagagaa aaagtagta cctgaaaata ctataagaat aaatgaaaaa     540
aagagagatg ttttgtaag tgctagtatt caaactgata taaaaagtaa tcaagttaaa     600
ttatctagtt ctgtattaga aaaccagat gagaaaagtg atgttactga tacagcgtgt     660
acaggtagta ctaaggataa atctgtagag gaaaaagtag tacctgaagg tgatactata     720
agaataaatg aaaaaaagag agatgttttt gtaagtgcta gtgctcaaac tggtgatatg     780
aaaagtgatc aagttaaatt atctggttct agattagaaa aactagatga gagaaaggat     840
gttactgata caggttgtgc aggtagtact aaggacaaat ctgtagagaa aaagtagta     900
tctgaaggta ctgctataag agatgaaaag gagagtagtg ttgctagaag tgttggtgtt     960
actttaatc ttcaaagtgg taatgtaaaa gatgataaag taaaactatc aggtgtagat    1020
ttaggtaaaa tagaggattc agttttatct gcttctagtt gtgaaactac tgttaaggat    1080
aataagcctg ttatatgtgt tggaaaagaa agtacgttc aattagcttc aagtttggat    1140
ttggttaata ctgttgaaga tagttcaaga aatactcgtg gttaagtga aacttgttct    1200
ttaatgttag attttgacag aaatggtaat cctgtatacg aagaggcaac tagtaagtta    1260
gtgcctagtt tctatcctga taatgttata tatcacacta agaaaaaaca ttgtggtgtt    1320
gatcttcctc aatcagaaga tcaactttat tcatgtatta ctaatgtgca tagtcaatat    1380
gatgtgactg aaaatagtgt aagtgtatat ccgcgtgatt tggttcctga tgatataaaa    1440
caagctaaac agaatgaaga tactaaacag ggtgctttta tagctacagg ttctacaacc    1500
gcggctgcgc atagtcaata tgatgtgact gaaaatagcg taagtgtatg tcagagtgat    1560
ttggttcctg atgatataaa acaagctaaa cagagtgaag atactaaaca gggtgctttt    1620
atagctacag gttctacaac cgcggctgcg catagtcaat atgatgtgac tgaaaatagt    1680
gttagtgtat atcagagtga cttagtttct gataatataa acaagctaa acagaatgaa    1740
gatactaagc agggtgcttt tatagctaca ggttctacaa ccgcggctgc gcatagtcaa    1800
tatgatatga ctgaaaatag cgtaagtgta tgtcagagtg acttagttcc tgatggtgta    1860
aaacaatcta aacagcatga agatactaag cagggtgctt ttatagttac aggttctgta    1920
tctgctaagt tagatattgt tgatgtagtt agtttagggg aaaaacgtga tattgatgaa    1980
aaagttgtta agtcatcagg ttgtactact gctgattcag ttagtaatcc tgtaggtatg    2040
gataaagttc aatattgtgt acctgactta gagatgagag taaaatgga tcttgtagaa    2100
gatcaccata atatggctag tatggaaaaa tgttatcctg atagagaagt tgttgagcaa    2160
ttaagtaatg ttactacttg tttggttagt actccagtaa ttgaacatag agttcatagt    2220
gttgagtctg ttgcagagtt acaagtaaaa ataggtcctt tagatgaggg aaaatgtaaa    2280
```

-continued

```
gacagtgtgg taaggagctc atcatttact agtgatacat gtttaaaaga tacaggtgca    2340
acaatgactg tagaagaata tggtaataaa cctagtacag gtctttgtgc tagtaggggt    2400
gatgatagtg tttcttctat gattggtata ggttcgtatt ttatagataa gatgatttgt    2460
gatattgata ctactgtgca gcttaataat acattttcta ctttagaaaa agaaaaaac    2520 tgttttatag ataatattaa aaaaaataat gaaaaatat ttagtaaccct tgttaatatt    2580 atggatttaa taaagaaac ggtaggtatt caatttttg atactaaaag tacagatgat    2640
atatccaggt atgtaatgga acaatctagt ggtgtttatg atgatgttat gtcacaaatg    2700
cttatccaag atgaaaaata tttatttaag gtctttaaac atattattcc ggttttgct    2760 aaaatattct ttaacaatga tcctatatct tcaatggaat ggaaattagt agatgaattg    2820
ttctctatga aagggcagt cttacaagat aatgtgtatt ttcaaaggat attttattgt    2880
atagtgtgtg catgtgaaaa aactgcaggt acaataaaga aaattcagtc gttatctaaa    2940
cagtgtgatg aaatacgaga aaagattaaa agtgtaatc taaggcaagg aaagaagaaa    3000
agtgcattgt cgaaatttac agatcatttt agtgaaaaaa aggaagacct gttgtgttta    3060
ttagataaaa tagaaaaaga actgaattta actaagcaag tttacactaa tcttatagca    3120
gaaaaagagg cgttattaac aggagatgtt gcttatataa gatattttgt atcacgtatt    3180
gtttttgata gttggaaatt tgatgataag gctaaacagg ttgtcaaaaa tataaagaac    3240
ctagcaccat atgtgttatg tgatgtgttg tatgaagaag aaaaaaaata tctaggtttg    3300
gtgaagtgta ttgtttgtga gtacacggtt ttttataaag atatagataa tttttttacct    3360 atagttcaac aatatcatga tcgacgacaa tctagaagtg ctgcagccca aaaatttat    3420 gatcaggaaa ttgatggtgt tcttcctatg gatactttag aaggtgtagg ggatcttgta    3480
gctatggaat taggacaaaa cagtaaatgt aatgcacatt aa    3522
```

```
<210> SEQ ID NO 8
<211> LENGTH: 4122
<212> TYPE: DNA
<213> ORGANISM: Ehrlichia ruminantium

<400> SEQUENCE: 8
```

```
atgaatgaga taatcctata cacagcagta tcactgtttt ttatatgtat ttactatgtt     60
ctgcttgtgg ctaggtttgt gtgttatgtg ttaagtatta tgaagtataa gtcaagagaa    120
ttggatatat cggataatga tacaaaaagt agggttactt attgtagtca gagtgagtat    180
gaatatggaa agtacgagat ggaaacttta tctggaaaag atggtattga atttctaaaa    240
tcagtttacc atagtgatag tgatgatgta ggtgatgttt taaaatcaaa atctactgtc    300
tcatctacca aaatggatca ggtaacacat caaatttctg acgttcaaac tatagaacgc    360
gataatgtag aaggtcaaca agttatggtt aaggaaaatg ctggtgttgg tgttcactat    420
aatcatactg aaactattat aaaaacaagt cttagtttta atctgatgt tatggttgat    480 actaaggata atctctataga ggaaaaagta gtacctgaag gtgatactat aagaataaat    540
gaaaaaaaga gagatgtttt tgtaagtgct agtgctcaaa ctgatatgaa agtaatcaa    600 gttagattat ctggttctag attagagaaa ccagatgaga aagggatgt tactgataca    660 gcgtgtacag gtagtactaa ggataaatct gtagaggaaa agtagtacc tgaaggtgat    720 actataagaa taaatgaaaa aaagagagat gttttgtaa gtgctagtgc tcaaactgat    780
atgaaaagta tcaagttag attatctggt tctagattag agaaaccaga tgagaaaagg    840
gatgttactg atacagcgtg tacaggtagt actaaggata atctctataga ggaaaaagta    900
```

```
gtacctgaag gtgatactat aagaataaat gaaaaaaaga gagatgtttt tgtaagtgct    960
agtgctcaaa ctggtgatat gaaaagtgat cacattaaat tatctggttc tagattagag   1020
aaaccagatg agaaaaggga tgttactgat acagcgtgta caggtagtac taaggataaa   1080
tctgtagagg aaaaagtagt acctgaaggt gatactataa gaataaatga aaaaagagag   1140 gatgttttg taagtgctag tgctcaaact ggtgatatga aaagtgatca cattaaatta    1200
tctggttcta gattagagaa accagatgag agaagggatg ttactgatac aggttgtacg   1260
ggtaatacta aggataaatc tgtagaggaa aaagtagtac ctgaaggtga tactataaga   1320
ataaatgaaa aaagagaga tgttttgta agtgctagtg ctcaaactgg tgatatgaaa     1380
agtaatcaag ttaaattatc tggttctaga ttagaaaaac tagatgagag aaaggatgtt   1440
actgatacag gttgtacggg taatactaag gataaatctg tagagaaaaa agtagtatct   1500
gaaggtactg ctaagagag tgaaaaggag agtagtgttg ctagaagtgt tgatgctact    1560
tttaatcttc aaagtggtaa tgtaaaagat gataagtaa aactatcagg tgtagattta    1620
ggtaaaatag aggattcagt tttatctgct tctagttgtg aaactactgt taaggataat   1680
aagcctgtta tatgtgttgg aaaagaaagt acgtttcaat tagcttcaag tttggatttg   1740
gttaatgctg ttgaagatag ttcaagaaat acttgtggtt taagtgaaac ttgttcttta   1800
atgttagatt ttgacagaaa tggtaatcct gtatacgaag aggcaactag taagttagtg   1860
cctagtttct atcctgataa tgttatatat cacactaaag aaaaacattg tggtgttgat   1920
cttcctcaat cagaagatca actttattca tgtattacta atgtgcatag tcaatatgat   1980
gtgactgaaa atagtgtaag tgtatatccg cgtgatttgg ttcctgatga tataaaacaa   2040
gctaaacaga tgaagatac taaacagggt gcttttatag ctacaggttc tacaaccgcg    2100
gctgcgcata gtcaatatga tgtgactgaa aatagcgtaa gtgtatgtca gagtgactta   2160
gttcctgatg atataaaaca agctaaacag aatgaagata ctaaacaggg tgcttttata   2220
gctacaggtt ctacaaccgc ggctgcgcat agtcaatatg atgtgactga aaatagtgtt   2280
agtgtatatc agagtgactt agttcctgat gatataaaac aagctaaaca gaatgaagat   2340
actaagcagg gtgcttttat agctacaggt tctgcaaccg cggctgcgca tagtcaatat   2400
gatatgactg aaaatagcgt aagtgtatgt cagagtgatt tggttcctga tgatataaaa   2460
caagctaaac agaatgaaga tactaagcag ggtgctttta tagttacagg ttctgtatct   2520
gctaagttag atattgttga tgtagttaat ttaggggaaa aacgtgatat tgatgaaaaa   2580
gttgttaagt catcaggttg tactactgct gattcagtta gtaatcctgt aggtatggat   2640
aaagttcaat attgtgtacc tgacttagag aggagagtga aatggatct tgtagaagat    2700 cactataata tggctagtat ggaaaaatgt tatcctgata gagaagttgt tgagcaatta   2760
agtaatgtta ctacttgttt ggttagtagt ccagtaattg agcatagagt tcatagtgtt   2820
gagtctgttg cagagttaca agtaaaaata ggtcctttag atgagggaaa atgtagagac   2880
agtgtggtaa tgagctcatc atttactagt gatacatgtt taaagatac aggtgcaaca    2940 atgactgtag aagaatatgg taataaacct agtcacaggtc tttgtgctag tagggtgat    3000 gatagtgttt cttctatgat tggtatgggt tcgtatttta tagataagat gatttgtgat   3060
attgatacta ctgtgcagct taataataca ttttctactt tagaaaaaag aaaaaaacat   3120
tttatagatg atattaaaaa aaataatgaa aaaatattta gtaaccttgt taatattatg   3180
gatttaataa aagaacggt aggtattcaa tttttttgata ctaaaagtac agatgatata   3240
tccaggtatg taatggaaca atctagtggt gtttatgatg atgttatgtc acaaatgctt   3300
```

```
atccaagatg aaaaatatttt atttaaggtc tttaaacata ttattccggt ttttgctaaa      3360 atattctttta acaatgatcc tatatcttca atggaatgga aattagtaga tgaattgttc      3420
tctatgagaa gggcagtctt acaagataat gtgtattttc aaaggatatt ttattgtata      3480
gtgtgtgcat gtgaaaaaac tgcaggtgca ataagaaaaa ttcagtcatt atctaaacag      3540
tgtgatgaaa tacgagaaaa gattaaaaag tgtaatctaa ggcaaggaaa gaagaaaagt      3600
gcattgtcga aatttacaga tcattttagt gaaaaaaagg aagacctgtt gtgtttatta      3660
gataaaatag aaaagaact gaatttaact aagcaagttt acactaatct tatagcagaa       3720
aaagaggcgt tattaacagg agatgttgct tatataagat attttgtatc acgtattgtt      3780
tttgatagtt ggaaatttga tgataaggct aaacaagtta tcaaaaatat aaagaaccta      3840
gcaccatatg tgttacgtga tgtgttgtat gaagaggaaa aaaatatct aggtttggtg       3900 aagtgtattg tttgtgagta cacggttttt tataaagata tagatgattt tttacctgcg      3960
gttcaagaat atcataatcg acgacaatct agaagtgctg cagcccgaaa attttatgat      4020
caggaaattg atggtattct tcttcctatg gatactttag aagatgtagg ggatcttgta      4080
gctatggaat taggacagaa cagtaaatgt aatgcacatt aa                          4122
```

<210> SEQ ID NO 9
<211> LENGTH: 2856
<212> TYPE: DNA
<213> ORGANISM: Ehrlichia ruminantium

<400> SEQUENCE: 9

```
ttgcataaaa tcatgcttac atcacttaaa actacagtta ctgataataa actaagatct       60
agtattatta atggatctag tgttaatttt tttaaaaaag gcaacattat tttttctgta      120
tattatacaa gaaataatgt taatggatat gatgtaatat gtgagattca acatggtgct      180
tctatttatt atatgaaaat taatgatcat gcaattattg atcgtcggac aacaaattat      240
ccaccagaga tgttatttgt aaagaatagt aatgatgatt tgatatttat tgttattcct      300
gaagaaagta aaggtcgtaa agctttagtt atcaaaatat ataagataaa ttataatcct      360
aatgtgtctt tatccaaatt acatgactta caattaatta gttgcaataa ctatctcaaa      420
gaagaagtga atatcctat tattttacat caggatacgg tggtaggat tgttgttatt        480 gcaagagtag ataatgacta tcgaggtgat gttacagata gattgtatgt gatgtggcaa      540
ttgagatatc ataataatag atttgaaatt ataggtttaa gtaatgggta taggcaattt      600
aatgctgcct atttatttaa gcattctggt tatattaatc gtggtaaatg tcatgataga      660
ctaattgtta aattaggatc ggatagtttt ataaattttc tttatgttgg gaaacatatt      720
tctagagatt acaatttttt ttctagtata tatgattat ctataaatta taatatgcat       780
cttgatccag aagaatgttt ggtgggttct ttttatggtt gtaatgctag tagtggtagg      840
aaatataata ttcctaatag ctgtattcat gttattgata tttttcgtga tgatgggaat      900
gtatatatag catatattgg tactgtattt aatagtacat ttaagaataa aaagcagttg      960
gttattgttt atactatggg tgatgaacaa tcgcctgtgt atgatttat gcagattaca      1020 gaagatatta gtgccatata tataaattct actgaaaata ttttagcaat aacgactatg      1080
ggaagtgatt atcttgtaaa atatgagatt tcaaaattac agttaaaatt agggattgtt      1140
gatcatgttg atgttataaa aattccacgt aatgtagtga aaaatattgc taattttaca      1200
tatgttgttg atacagtttt aggtttgat agtgttgaac atattaatat tcgtaatgta      1260
ttagctacaa aatcaactgt taatgataaa gtatctcagt ttttttaaa tattagagaa       1320
```

```
atggaatttg gtgatttatt taagagttgg agtggtgaat ataatgactt gttaataggt    1380
tatactatgc ctgctagtta tggtgtaaat tatactacag aatatttaag cgatgttata    1440
actgtttcag gtaatgcagg ttttgtagag aagttcatat caactagtaa atgggtgat    1500 gtatttaaga ttacagataa cttaattaat tatactagtg taaaccctac taatcatatg    1560
gcacatgtga cattgcaatc aaaattatca gatggtgagg gtattacaga gcgtgcgggt    1620
aatagatcag ataattctgt aagtgaaagt ttagctacag gattggttct tactagtaaa    1680
agtgatgatt tgtttaaaag tacggctagt cctattaatc atgcttttgg ttatgtaata    1740
aagcctacta tccacgtaac gcatgttaca ttgcaaccga gtcaccata tggtaaagag    1800 gttgtgaggc atataaatcc taaaacggat aattctatac atacaagttc aataccaaga    1860
tcaatactga ctaatagaag cgatggtgta tttaaaagta cagctagtcc tattaatcat    1920
gcttttggtt atgtaataaa gcctactcgc catgtaacgc atgttacatt gcaaccgaag    1980
tcaccatatg gtaaagaggt tgtgaggcat ataaatccta aaacggataa ttctatacat    2040
acaagttcaa taccaagatc agtactgact agtaaaagct atgatgtatt taaaagtacg    2100
gctagtccta ttaatcatgc ttttggttat atgaaacctg ctagttctgt tgtagtgcca    2160
ttaggtgata ctgatgtttc aaagcaagtg gaaagtgtta gtaatgttcc agtacatctt    2220
actcctacag taagatcagt attagtaggg gatgcgtatc atgtatctgg cagtgaaaaa    2280
gatagtgttg gacatgaaca agatttgggt catggtgatg ttagtactga tgttgtattg    2340
aaactaatga gtgataatgt atccaacaat attagtaggc atgtgaataa ttctttagct    2400
ataaaacata agatattagg tagaaaagta agtataata taaggcgtag tactgttaga    2460
tctggtgtta atattcgcaa taaaagtaca gtgagtacaa gatatacatc tcatggcata    2520
caagaggcta ataatatgaa tgttacattg tttaatccta cacagcataa tattagtagt    2580
tataatggta gttattaaaa tagtaattct gcttttaata ctgaaagttc tgttgattat    2640
aaagtagtaa ttgcagtaat atctagtata ctgcttatct tttattatt aggtggattt    2700 aaatgtataa agtggtattt agcaaagttg aatagaagaa ggatgtctaa taatgaacag    2760
ggatttgtga tttttaattt ggatagtatt caaagtagtg tttctggtgt gcaagtgaca    2820
aaaggtacca catctcgaat agagagtcta ttctag                              2856
```

<210> SEQ ID NO 10
<211> LENGTH: 1659
<212> TYPE: DNA
<213> ORGANISM: Ehrlichia ruminantium

<400> SEQUENCE: 10

```
atgttattca aacccggttt acccatttcc aagattacag aatctctgca tagatcagtt      60
atacgtgagt tgaatagagc gtcagaaata catgttaata cgtgtcattg tataggagct     120
acaataaata aaaaaactct taatatctgc gttgataata agccaggtaa tcggtgtact     180
ccagtaggaa catctttatt tcgtatggaa tgtattatac ccgctcctgt aataaataat     240
ccacgtaata tatctttaca aaagttgaca caagtattgt ctagtccttt tttaataaca     300
ctagaaccac ttaaggttga tgcatatttt attgtaccag aggaagaatt aaagaatttc     360
atagatttag taaaaccttt atctagtatg ccacgtgaag gacttttacc tatttataat     420
attggtaaat tcggaacatt ttccttatgt aggccaaaaa gtataggtaa tagagatgta     480
aggcatgatg taccatttga cgaattcaaa gcttttaata tttaggagg tctagaggat     540 tctatttttt ttaaaacacc ctcatcaatc cctgatatca caaaacgtaa tacaaaacaa     600
```

| | | |
|---|---|---|
| agcatagcag atagtaaaca acaaaaagtt gtagtaactg gtaaggaaat tcaacacaaa | 660 |
| atacaacata taaaaaaaat gttttctaga gtttctacta cacaatgttc accttcaagt | 720 |
| acaccagtca gtgctcaaat gacacataat atagaagaaa aaacagcaag tagtccgcaa | 780 |
| aagccagcta tccaaaaggt tatagtaact agcaaacaac ctcgtaaaga agaaatacaa | 840 |
| tttatatata caaagtttcc tgaggctcca agaacatt catcttcaaa tcaaacacaa | 900 |
| gagacaacaa gcaagcattt agaacagcat ctatcaaaaa gtatagtagg tggtgcgcca | 960 |
| cttatacaaa aaggtacagt agatcctcaa caagttgtca gaccaaaaac atttgcatct | 1020 |
| agtccttttt ataaagaatc gacacttcca actacaaaat atccatcttc aaatcaaaca | 1080 |
| caagaaacag caagcaagca tttagaacag catccatcaa aaattacaca aaaaggtaca | 1140 |
| ataaaccttc aacaagttgt tagaccaaaa acacaatttt catctagtcc tttttataaa | 1200 |
| gaacaggtac ttccaaatat aaaacatcca tcttcaaatc aaagacaaga gacagcaaac | 1260 |
| aagcatttag aacagcgtac attaaaaaaa agtacactag gtagcatgcc gccatctata | 1320 |
| caaaaaggta caatagatcc tcaacaagtt gttaggccaa aaacacaatc tgcatctagt | 1380 |
| ccttttaca aagaatcgac acttccaact acaaacatc aaatgttaag tgttatagaa | 1440 |
| gaatcgacaa atagtagtgt accaattaat acattaagtt ctgaagaaat accacggttt | 1500 |
| ttcagtgtag attattttag tagttataaa gtattgtacg atacttacaa agaatcttat | 1560 |
| aaagttgata ctttaccaac agcacctctc gtcccatcat gtcaacttga agatgatgta | 1620 |
| tttgttgaaa atagtaatcc ccatgtatct ttgaattaa | 1659 |

<210> SEQ ID NO 11
<211> LENGTH: 873
<212> TYPE: DNA
<213> ORGANISM: Ehrlichia ruminantium

<400> SEQUENCE: 11

| | | |
|---|---|---|
| atgccactta ctttcgatct atatgcacat gaaaaagat taaatcttct tctatgcaat | 60 |
| gctataaatt ccgctgctaa tctagttaat gaaatagata tatcttgtgt aggatatact | 120 |
| gatgaaaccg gtaaattagt ggcttttatt gaccctaaca ttccactaaa cttattccct | 180 |
| attcctcaaa atctatcctt atttcgtata agtggtacta taccaattac cattataaca | 240 |
| aattctaatt ctcaagaatt atctaaagag tttgttttca cagaaggtga ataaatagt | 300 |
| ggccttgtta agtgtgaaat gtattgttta gtaggtaatg aaaatcttga tgattttact | 360 |
| gaaatatgta gtaatcctaa aataggatat gaaaatttaa taaaaatttc caataatatt | 420 |
| tacacacaat tatttacaga agatatatta aaatttccta ttaacataga acatgctcta | 480 |
| tcaaatatag caaatttaaa tgcagaatat atatatgcat ctgatctagt aaggaaagaa | 540 |
| aaacttaagc agcttaaaga agaaatgat gatttatgta atgcaatatg ccatgcatgt | 600 |
| aatgaggaga atgtaacttc tgtaaaatgc ataggacata ctcctgacag taatcaactc | 660 |
| acagttcata ttaaatgtcc agaaagcctt ttacctatac ctcaaagtaa ctctctattt | 720 |
| cttgtcgaga tgagtatatt acctaatgtt ataggggggca atcaaatatt atcctctact | 780 |
| tttgaattaa cagaaagtga atgtaaaaaa ggtgctctca attgtacaat gtactgttta | 840 |
| gttagtaagg agaaacttaa aaaattttac tga | 873 |

<210> SEQ ID NO 12
<211> LENGTH: 1740
<212> TYPE: DNA
<213> ORGANISM: Ehrlichia ruminantium

<400> SEQUENCE: 12

```
atggctatac cacacactat tatagcaaat aatgccatat tatcttctac tttttaaagta      60
gtaaaaaatg atcttggtat tgatagtgat tatattttat gcactgcata ctgtctagta     120
actaagcata atcttcaaga ttttactaat gaagtgtcat cggatgatgt aatagatgat     180
actacacaac aaaaacgtca aaaatttaaa aatatcatta aattatgttc tgtaaaatgt     240
gtaacattac atacacaaga aatgttatca ttaaacatta gtgaagaaga actaatcaac     300
gatatagggt tatgtaatgc aactttcaaa tatttaagta atctgcatca agaaaagatt     360
gatatactta gacaagcaaa taataaatta tgtcgtgaaa tatgtcttaa acttaataaa     420
catcaaacaa actatataag atgtatagga aatactgttg ataatcaatt aatagttacc     480
actcagtgtc cacgagatct tcttcctttt cctaaaaatc aatctttatt cattataagg     540
ataaatatac cacctaacat tatattcac agtaaaatac taaataatac atttaaatta     600
acaaaaagtg aaaagaaga ttattacatt aaatgtgata tgtattgcct agtatatgaa      660
gaagatatta agagttttat tgatgtatgt gatgatttag ataagccata tattgaagag     720
ttaattcaac attgttctgt aaaatgtata aaattgtata cacaagaaat gttatcatta     780
aacattagtg aagaagaact aatcaacgat agggttat gtaatgcaga gtttaaatat       840
gttgaaagta gacagataat tgaatcagta ctagacacat tgagtatat cgaaatacaa      900
gcaaataaac tcctatgcag aattttgcct acactttgtg ctttatataa aaaagatttt     960
ctcatcaaaa agatacgttg tataggtaat actatagatc ctgaacaagg attaacaatt    1020
tatcctccta gtatattctc aaaggaacac ttaccaactg ccaaaggtac atctttattt    1080
ttaatacgaa gtaggatgtt aactgaagtt atattaagta ctcctgaact agtgaatgta    1140
cataatctaa gtgatgaaga aatgtcgagt aagtatttat tatgtgatat atattgccta    1200
gtagataatc aaaacattaa tctatttaag aatctttgta caaagacaag acagttttct    1260
gatgttgtaa ttacatgtga tgtaagatat attaggatat atacaaaaga tgctagaaaa    1320
ttcccatttta atgaggcaag tgtattaaaa caattaggaa atataaaagg aaaatatctc    1380
aatgaacaag actttaaagc attagttagt tctggacttt atactaaatc agcaagtgaa    1440
tcttcatcag cagtatcaac tgaagaagaa tcaattatac aacaagaact ccatgtaaaa    1500
cagagtttaa atcaagatt atcacaaata agaaaacaac taacacctga ttcttcatca    1560
tctaatacag tatcaagtga agatgatata gatacaccag cagaaattaa aagaaaaaga    1620
gaagcaagac gtttaaaatt agcaaaatta caacaagaag aatcacaaac aacaggaata    1680
ggtatgttgt ctgatcaaga agtttcacat cataaatctc aaagtaaaga tttagattag    1740
```

<210> SEQ ID NO 13
<211> LENGTH: 3252
<212> TYPE: DNA
<213> ORGANISM: Ehrlichia ruminantium

<400> SEQUENCE: 13

```
ttgcataaaa ttatgcctac atcacttaaa accatagtta ctgatagtaa actaagatct       60
agtattattg atggatctag tgttaatttt tttaaaaaag gtaacattat tttttctgta      120
tattatacaa gaaataatgt tgatggatat gatgtaatat gtgagattca acatggtgct      180
tctatttatt atatgaaaat taatgatcat gcaattattg atcgtcgggc aacgaattat      240
ccaccagaga tgttatttgt aaagaatagt aatgatgatt tgatatttat tgttattcct      300
gaagaaagta aggtagtaa agctttagtt atcaaaatat ataagataaa ttataatcct      360
```

```
aatgtgtctt tatcccaatt acatgattta caattaatta gttgcaataa ctatctcaaa    420
gaagaagtga aatatcctgt tattttacat caggatacgg ttggtaggat tgttgttatt    480
gcaagagtag ataatgacta tcgaggtgat gttacagata gattgtatgt gatgtggcaa    540
ttgagatatc ataatagtag atttgaaatt ataggtttaa gtaatgggta tagacgattt    600
aatgctgcct acttatttaa gcattctggt tatattaatc gtggaaaatg tcatgataga    660
ctaattgtta aattaggatc ggatagtttt ataaattttc tttatgttgg gaaacatatt    720
tctagagatt acaattttt ttctagtata tatgatttat ctataaatta taatatgcat    780
cttaatccag aagaatgttt ggtgggttct ttttatggtt gtaatgctag tagtggtagg    840
agatataata ttcctaatag ctgcattcat gttattgata ttttcgtga tgatgggaat     900 gtatatatag catatattgg tactgtattt aatagtacat ttaagaataa aaagcagttg    960
gttattgttt atactatggg tgatgaacaa tcgcatgtgt atgattttat gcagattaca    1020
gaagatatta gtgccatata tataaattct actgaaaata ttttagcaat aacgactatg   1080
ggaagtgatt atcttgtaaa atatgagatt tcaaaattac agttaaaatt agggattgtt    1140
gatcatgttg atgttataaa aattccacgt aatgtagtga aaaatattgc taattttaca    1200
tatgttgttg atacaatttt agggtttgat agtgttgaac atattaatat tcgtaatgta    1260
ttagctacaa aatcaactgt taattataag gtatctcagt tttttttaaa tattagagaa    1320
atggaatttg gtgatttatt taagagttgg agtggtgaat ataatgactt gttaataggt    1380
tatactatgc ctgctagtta tggtgtaaat tatactacag aatatttaag cgatgttata    1440
actgtttcag gtaatgcagg ttttgtagag aagttcatat caactagtaa aatgggtgat    1500
gtatttaaga ttcagataaa cttaattaat tatactagtg taaaccctac taatcatatg    1560
gcacatatga cattgcaatc aaaattgtca gatggtgagg gtattacaga gcgtgcgggt    1620
aataaatcag ataattctgt aagtgaaagt ttagctacag gattggttct tactagtaaa    1680
aatgatgatt tgtttaaaag tacagctagt cctattaatc atgcttttgg ttatgtaata    1740
aagcctactc gccatgtaac gcatgtaaca ttggaatcga agtcaccata tggtaaagag    1800
gttgtgaggc atatgaatcc taaaacggat aattctatac atacaagttc aataccaaga    1860
tcagtactga ctagtagaag cgatgatgta ttgaaaagta cagctagtcc tattaatcat    1920
gcttttggtt atgtaataaa gcctactcgc catgtaacgc atgtaacatt ggaatcgaag    1980
ttaccatatg ataaagaggt tgtgaggcat atgagtccta aaacggataa ttctatacat    2040
acaagttcaa taccaagatc agtactgact agtaaaagcg atgatgtatt gaaaagtaca    2100
gctagtccta ttaatcatgc ttttggttat gtaataaagc ctactcgcca tgtaacgcat    2160
gtaacattgg aatcgaagtt accatatgat aaagaggttg tgaggcatat gagtcctaaa    2220
acggataatt ctatacatac aagttcaata ccaagatcag tactgactag tagaagcgat    2280
gatgtattga aaagtacagc tagtcctatt aatcatgctt ttggttatgt aataaagcct    2340
actcactatg taacgcatgt aacattggaa tcgaagtcac catatggtaa agaggttgtg    2400
aggcatatga atcctaaaac ggataattct atacatacaa gttcaatacc aagatcagta    2460
ctgactagta aaagcgatga tgtattgaaa agtacagcta gtcctattaa tgatgctttt    2520 ggttatgaa acctgctag ttctattgta gtatcattag gtgatactga tgtttcaaag     2580
caagtgaaaa gtgttagtaa tgttccagta tatcttactc ctacagtaag atcagtatta    2640
gtaggtgatg cgtatcatgt atctggtagt gaaaagagata gtattggaca tgaacaagat    2700
ttgggtcatg gtgatgttag taccgatgtt gtattgaaac taatgagtga taatgtatca    2760
```

```
aacaatatta gtaggcatgt aaatgattct ttagctataa acataagat attaggtaaa      2820 aaaataaagt ataatataag gcgtagtact gttagatctg ctgttaatat tcgcaataaa     2880
agtacagtga gtacaagata tacatctcat ggcatacaag aggctaataa tatgaatgtt     2940
acattgttta atcctacaca gcataatatt agtagttata atggtagttt attaaatagt     3000
aattctgctt ttaatactga aagttctgtt gattataaag tagtaattgc agtaatatct     3060
agtatactgc ttatctttt attattaggt ggatttaaat gtataaagtg gtatttagca      3120
aagttgaata gaagaaggat gtctaataat gaacagggat ttgtgatttt taatttggat     3180
agtattcaaa gtagtgtttc tggtgtgcaa gtgacagaag gtaccacatc tcgaatagag     3240
agtctattct ag                                                         3252

<210> SEQ ID NO 14
<211> LENGTH: 1836
<212> TYPE: DNA
<213> ORGANISM: Ehrlichia ruminantium

<400> SEQUENCE: 14
atgttattca aacccggttc acccgttgcc aagattacag aatctctgca taaatcagtt       60
atatatgagt tgaatagagt accagaaata catcttaata catgtcattg tataggagct      120
acaataggta caaaacttga tatctggatt gataataagt caggtcatcg gtgtactcca      180
gtaggaacat ctttattct tatggaatgt attataccca ctgctgtaat aaatcatcca       240
cgtaatatat ctttacaaaa gttgacacaa gtattgtcta gtcgcttttc aagaacacaa      300
ccacttaagg ctgatgtata ttttattgta tcagaggaag aattcgagaa tttcagaagt      360
acagtatccc cttatgtag tatgggactt aatgaacttt tacctgttta taatattggt       420
aaattcggag cattttgcgt atgtaggcca aaaagtatag gtaatagagg tgtagatgta      480
ctatttgatg aatacaaagc tttaagggtt ttaggaggtc tagaggattc taatttttt      540 aaaacacct tatcaacctc taataccaca aaacgtaata caaaacaaag cacagcaaat      600
aatagagaac aaaatttgt agtaactggt aagaaaattc aaagcaaaat acaaagtata      660
aaacatctac ataaaatatt ttctagatct tctactacac aatgttcacc tttaagtaca      720
ccagtcaata ctaaaacaca acataatata gaagaaaaaa cagcaagtag tacgcaagaa      780
ccaaatatcc aaaaggttat agtaactagc aatcaaccta atagagaaaa aacacaactt      840
atatgtacaa agtttcctga ggctccaaaa tatccatctt taaatcaaag acaagagaca      900
ggaggcaagt atttagaaca gcgtctatca aaagtacag cagatagtac gccatttaca       960
caaaaaggta caacagattc tcaacaagtt gttagaccaa aaacacaatt tgcatctagt     1020
cctttttatt tttatcaaga acagccactt ttaactacaa acattcatc ttcaaatcaa      1080 agacaagaga caggaggcaa gtatttagaa cagcgcctat caaaaagtac agcagatagt     1140
acgccattta cacaaaaagg tacaacagat tctcaacaag ttgttagacc aaaaacacaa     1200
tttgcatcta gtccttttta tttttatcaa gaacagccac tttaactac aaaacattca     1260 tcttcaaatc aaagacaaga gacaggaggc aagtatttag aacagcgcct atcaaaaagt     1320
acagcagata gtacgccatt tacacaaaaa ggtacaacag attctcaaca agttgttaga     1380
ccaaaaacat ttgcatctag ttctttttat aaagaatcgg cacttgcaat tacaaagcat     1440
ccatcttcaa atcaaagaca agaggcaaca acaagcatt tagaacagcg tccatcaaca      1500 aaagtacag tagatcctca acaagttgtt aggccaaaaa cacaatctgc atctagtcgt     1560
gtttataaag aacagggact tccaactaca aaacataaaa tattaagtgc tataaaagaa     1620
```

| | |
|---|---|
| tctacagata gtagtacatc agttaataca ttaagttctg aagaagattt acggttttta | 1680 |
| aatgtagatt attctagtag ttgtgaaata ttatacgata ctttcagaga atcttataga | 1740 |
| gttagtgctt taccaacatc acctctcatc ccatcacatc aacttgaaga tgatgtatttt | 1800 |
| gttgaagatg gttatcctcg tgcatcttat ctttga | 1836 |

<210> SEQ ID NO 15
<211> LENGTH: 3570
<212> TYPE: DNA
<213> ORGANISM: Ehrlichia ruminantium

<400> SEQUENCE: 15

| | |
|---|---|
| atgccactta cttttgatct atatgcatat gaaagaaaat taaattttct tctatgcaat | 60 |
| gctgtaaatt ctaatcctaa gttagttaat gtaataaatg tagtttgtgt aggatatact | 120 |
| gatgaaaata atcagttatt acttgctact gactacaaca ttccaccaga attcacccct | 180 |
| attcctagaa atcaatcctt atttcgtata atgctaata taaaaactag cattataaca | 240 |
| aattctttta gattatctca agagtttgct ttaacacaag aggagctaaa taatggtaat | 300 |
| gttaagtgtg aaatgtattg tttagtaggt aatgaaaatc ttgatgattt tactaaaata | 360 |
| tgtagtaagc ataaagtaag atataaaaat ctaacaacaa tttccaagaa tatttacaca | 420 |
| caattattta cagcagatat attaaaattt cctattaaca tagaacatgc tctatcaaat | 480 |
| atagcaaatt taaatgcaca atatatatat gcatctgatc taataaatga atctgatcta | 540 |
| ataaatgcgt ctgatctaat aaatgcgtct gatctaataa agaagaaaa attaagaat | 600 |
| attagaggaa gtactagtat attatatgat gcaatatgca gtacatatgc aactaatgat | 660 |
| taccatgtac tttctgtaaa atgcatagga tatactcata ataatcgaca actcatagtt | 720 |
| cacactcaat gtccagagaa ccttttacct atacctcaaa gtaactctct atttattgta | 780 |
| tgtgttgata tatcaccaga tatcataaca aataatgaaa atttatcctc tacttttgaa | 840 |
| ttaacagaaa gtgaaagtaa acaaagtact atcaattgtg caatgtactg tttagttaat | 900 |
| gatgaacaac ttggaagttt tactcataaa tgtaatacta caaataataa accaaagctt | 960 |
| caagatatta ttcaattttg ttctgtaata tgtataacac tcaatacaga aagaatatca | 1020 |
| tcattacaaa ttagcgaaga gagctaataa aatagtgtag gaataggtga tgtaacattc | 1080 |
| agaaatttta gtgatctacg taaggaaaaa cttaagaaaa tacagcaaat aaagaatgaa | 1140 |
| ctatgtagtg caatatgcag tatatatgca gctaataact accatgtact ttctgtaaaa | 1200 |
| tgcataggat atactcataa taatcaacaa ctcatagttc acactcaatg tccagacagc | 1260 |
| cttttaccta tacctcaaag taactctcta tttattgtaa atgttgatgt atcaccagat | 1320 |
| atcataacaa ataataaaaa attatcctct acttttgcat taacagaaag tgaaagtaag | 1380 |
| caaagtactc tcaagtgtgc aatgtactgt ttagttaatg atgaacaact tgaaagtttt | 1440 |
| actcataaat gtgatattac aaataataaa ccaaggcttc aagatattat tcaattttgt | 1500 |
| tctgtaatat gtataacact caatacagaa agaatgttat cattacaaat tagcgaagaa | 1560 |
| gagctaataa atagtgtagg aataggtgat gtaacattca aaaattttag tgatctacgt | 1620 |
| caggaaaaat ttaataaaat acagcaaaca ataatgaac tatgtagtgc aatatgcatt | 1680 |
| tcacctgaag aaaataaaat aattgatata aaatgcgtag gacacactac cgctaagaat | 1740 |
| aaattagtag ttcatactga atgtccacta gctcttcttc ctacacctca aggtgattca | 1800 |
| ttattttcta tactgatggc tataccatac gctattatag caaataatgc catattatct | 1860 |
| cctgctttta aagtagtaaa aaatgatctt ggtattaata gtaattatat tttatgcact | 1920 |

```
gcatactgtc tagtaactaa gcatgatctt caagatttta ctaatgaagt gtcatcggat    1980
ggtgcaatag gtgatagtat acaacaaaaa cgtcaaaaat ttgaaagtat cattaaatta    2040
tgttctgtaa aatgtgtaac attacataca caagaaatac tgtcattaaa tattagtcaa    2100
aaagaactaa tcaacgatat agggttatgt aatgcaactt tcaaatattt aagtaatctg    2160
catcaagaaa agattgatct acttaaacaa gtaataataa aattatgtcg tgaaatatgt    2220
aataaactta ggaaacataa aacacaatat ataagatgta taggaaatac tgttaatact    2280
aaattagtag ttaccactca gtgtccacga gatcttcttc cttttcctaa aggtcaatct    2340
ttattcatta taaggataaa tatatcacct aacattatat tacacagtaa aacactacgt    2400
aatacattta aattaacaac aagtgaaaga tcagatcatc acattaaatg tgatatgtat    2460
tgcctagtat atgaagaaaa tattaagagt tttattgatg tatgtgatga tccaaataag    2520
ccatatattg aagagttaat tcaatattgt tctgtaaaat gtataaaatt gtatacacaa    2580
gaaatgttat cattaaacat tagtgaagaa caactaatca acgatatagg gttatgtaat    2640
gcagaattta aatatgttga aagtaaacat ataattgaat cagtattgga cgcatttaat    2700
tatatcgaaa tacaagcaaa taaactccta tgcggaattt tgcctacact ttgtgcttta    2760
tataaaaaag attttctcat caaaaagata cgttgtatag gtaatactat agatcctgaa    2820
caaggattaa caatttatcc ttctagtata tacccaaagg aattcttacc aactgcccaa    2880
ggtacatctt tattttttaat acgaactagg atattaactg aagttatatt aagtactcct    2940
gaactagtga atgtacatat tctaaatgat gaagaaatgt tgaataagta tttattatgt    3000
gatatatatt gcctagtaga tgagaaaaac cttagaatat ttaagaatct ttgtacaaaa    3060
gcaagaaatc tttcagatat gataattaca tgtggtgtaa agtatgttag gatacataca    3120
aaagattcta aaagatttcc atttgatgaa gcaaaggtat taaaacactt aggaggtata    3180
gacggaagat atctcgacga aggagatttt gacaaattac ttagttctgg actttatacc    3240
aaatcatcaa gtaagtcttc atcaacaata tcgactgaag aagaatcaag tacacaagaa    3300
gggacccata taaaacgtag tttaagatca acattattaa aaataagaaa acaaatagga    3360
cctgagtctt catcatctgc tacattctca agtggagatg agttagattc agaagacgaa    3420
cttcaagaaa gaagacaaaa aagacgtgca agattagcaa gactacaaca tgaagaatca    3480
caaacaacaa aaagtaaaac aggaataggt ggtatcttgt ctgatcaaga gtttcacat    3540 cataaatctc aaagtaaaga tttagattag                                    3570

<210> SEQ ID NO 16
<211> LENGTH: 21
<212> TYPE: DNA
<213> ORGANISM: Ehrlichia ruminantium

<400> SEQUENCE: 16
atgagtcaca gttttattga g                                             21

<210> SEQ ID NO 17
<211> LENGTH: 21
<212> TYPE: DNA
<213> ORGANISM: Ehrlichia ruminantium

<400> SEQUENCE: 17
cactcaaaat cacaagaagt a                                             21

<210> SEQ ID NO 18
<211> LENGTH: 25
```

```
<212> TYPE: DNA
<213> ORGANISM: Ehrlichia ruminantium

<400> SEQUENCE: 18
atgtatttag tctatttagt agctg                                         25

<210> SEQ ID NO 19
<211> LENGTH: 23
<212> TYPE: DNA
<213> ORGANISM: Ehrlichia ruminantium

<400> SEQUENCE: 19
ataacatcta attgaacaat atc                                           23

<210> SEQ ID NO 20
<211> LENGTH: 20
<212> TYPE: DNA
<213> ORGANISM: Ehrlichia ruminantium

<400> SEQUENCE: 20
atgaaaggat ctttatctgc                                               20

<210> SEQ ID NO 21
<211> LENGTH: 20
<212> TYPE: DNA
<213> ORGANISM: Ehrlichia ruminantium

<400> SEQUENCE: 21
ccttcttctt cttcattatg                                               20

<210> SEQ ID NO 22
<211> LENGTH: 19
<212> TYPE: DNA
<213> ORGANISM: Ehrlichia ruminantium

<400> SEQUENCE: 22
aagaattaca tgatgcagc                                                19

<210> SEQ ID NO 23
<211> LENGTH: 22
<212> TYPE: DNA
<213> ORGANISM: Ehrlichia ruminantium

<400> SEQUENCE: 23
tcttctcttg ttatactctc tg                                            22

<210> SEQ ID NO 24
<211> LENGTH: 23
<212> TYPE: DNA
<213> ORGANISM: Ehrlichia ruminantium

<400> SEQUENCE: 24
atggatttaa ataaactaat aaa                                           23

<210> SEQ ID NO 25
<211> LENGTH: 19
<212> TYPE: DNA
<213> ORGANISM: Ehrlichia ruminantium

<400> SEQUENCE: 25
gcattttctc tacctacga                                                19

<210> SEQ ID NO 26
<211> LENGTH: 26
```

<212> TYPE: DNA
<213> ORGANISM: Ehrlichia ruminantium

<400> SEQUENCE: 26
gtacatagta tgtctttata taaaag        26

<210> SEQ ID NO 27
<211> LENGTH: 23
<212> TYPE: DNA
<213> ORGANISM: Ehrlichia ruminantium

<400> SEQUENCE: 27
ccaaatatat aaatgatcta ttc        23

<210> SEQ ID NO 28
<211> LENGTH: 25
<212> TYPE: DNA
<213> ORGANISM: Ehrlichia ruminantium

<400> SEQUENCE: 28
tccaccagag atgttatttg taaag        25

<210> SEQ ID NO 29
<211> LENGTH: 25
<212> TYPE: DNA
<213> ORGANISM: Ehrlichia ruminantium

<400> SEQUENCE: 29
caacagaact ttcagtatta aaagc        25

<210> SEQ ID NO 30
<211> LENGTH: 25
<212> TYPE: DNA
<213> ORGANISM: Ehrlichia ruminantium

<400> SEQUENCE: 30
gttaagtgtg aaatgtattg tttag        25

<210> SEQ ID NO 31
<211> LENGTH: 25
<212> TYPE: DNA
<213> ORGANISM: Ehrlichia ruminantium

<400> SEQUENCE: 31
cactttctgt taattcaaaa gtaga        25

<210> SEQ ID NO 32
<211> LENGTH: 25
<212> TYPE: DNA
<213> ORGANISM: Ehrlichia ruminantium

<400> SEQUENCE: 32
gtaggccaaa aagtataggt aatag        25

<210> SEQ ID NO 33
<211> LENGTH: 25
<212> TYPE: DNA
<213> ORGANISM: Ehrlichia ruminantium

<400> SEQUENCE: 33
caacaaatac atcatcttca agttg        25

<210> SEQ ID NO 34
<211> LENGTH: 25

```
<212> TYPE: DNA
<213> ORGANISM: Ehrlichia ruminantium

<400> SEQUENCE: 34
agggttactt attgtagtca gagtg                                25

<210> SEQ ID NO 35
<211> LENGTH: 25
<212> TYPE: DNA
<213> ORGANISM: Ehrlichia ruminantium

<400> SEQUENCE: 35
cctcttcgta tacaggatta ccatt                                25
```